(12) United States Patent
Vestgaarden

(10) Patent No.: US 8,162,981 B2
(45) Date of Patent: Apr. 24, 2012

(54) METHOD AND APPARATUS FOR SPINAL FACET FUSION

(75) Inventor: Tov Vestgaarden, Madeira Beach, FL (US)

(73) Assignee: VG Innovations, LLC, Winston-Salem, NC (US)

( * ) Notice: Subject to any disclaimer, the term of this patent is extended or adjusted under 35 U.S.C. 154(b) by 646 days.

(21) Appl. No.: 12/154,372

(22) Filed: May 22, 2008

(65) Prior Publication Data
US 2009/0036927 A1 Feb. 5, 2009

Related U.S. Application Data

(60) Provisional application No. 60/939,615, filed on May 22, 2007.

(51) Int. Cl.
*A61B 17/70* (2006.01)
*A61B 19/00* (2006.01)
*A61F 2/44* (2006.01)

(52) U.S. Cl. ..................... 606/247; 623/17.11

(58) Field of Classification Search .......... 606/246–249, 606/95–99, 76, 84, 86 A; 128/898; 623/17.11, 623/17.16
See application file for complete search history.

(56) References Cited

U.S. PATENT DOCUMENTS

| | | | |
|---|---|---|---|
| 3,848,601 A | 11/1974 | Ma et al. | |
| 4,501,269 A | 2/1985 | Bagby | |
| 5,015,247 A | 5/1991 | Michelson | |
| 5,389,080 A | 2/1995 | Yoon | |
| 5,484,437 A | 1/1996 | Michelson | |
| 5,505,732 A | 4/1996 | Michelson | |
| 5,522,899 A | 6/1996 | Michelson | |
| 5,569,290 A | 10/1996 | McAfee | |
| 5,593,409 A | 1/1997 | Michelson | |
| 5,609,635 A | 3/1997 | Michelson | |
| 5,741,253 A | 4/1998 | Michelson | |
| 5,772,661 A | 6/1998 | Michelson | |
| 5,776,199 A | 7/1998 | Michelson | |
| 5,785,710 A | 7/1998 | Michelson | |
| 5,797,909 A | 8/1998 | Michelson | |
| 5,860,973 A | 1/1999 | Michelson | |

(Continued)

FOREIGN PATENT DOCUMENTS
WO WO 2004/043278 5/2004

OTHER PUBLICATIONS

Stein et al., Percutaneous Facet Joint Fusion: Preliminary Experience, Journal of Vascular and Interventional Radiology, Jan.-Feb. 1993, pp. 69-74, vol. 4, No. 1.

(Continued)

*Primary Examiner* — Pedro Philogene
(74) *Attorney, Agent, or Firm* — Ronald E. Smith; Smith & Hopen, P.A.

(57) ABSTRACT

A spinal facet fusion implant comprising:
an elongated body having a distal end, a proximal end and a longitudinal axis extending between the distal end and the proximal end, the elongated body having a cross-sectional profile characterized by a primary axis and a secondary axis; and
at least one stabilizer extending radially outwardly from the elongated body in the secondary axis;
wherein the elongated body has a length along the primary axis which is less than the combined width of the spinal facets making up a facet joint;
and further wherein the at least one stabilizer has a width which is sized to make a press fit into the gap between the spinal facets making up a facet joint.

34 Claims, 33 Drawing Sheets

U.S. PATENT DOCUMENTS

| | | | |
|---|---|---|---|
| 6,080,155 A | 6/2000 | Michelson | |
| 6,096,038 A | 8/2000 | Michelson | |
| 6,120,502 A | 9/2000 | Michelson | |
| 6,123,705 A | 9/2000 | Michelson | |
| 6,149,650 A | 11/2000 | Michelson | |
| 6,206,826 B1 | 3/2001 | Mathews et al. | |
| 6,210,412 B1 | 4/2001 | Michelson | |
| 6,264,656 B1 | 7/2001 | Michelson | |
| 6,270,498 B1 | 8/2001 | Michelson | |
| 6,287,313 B1 | 9/2001 | Sasso | |
| 6,302,914 B1 | 10/2001 | Michelson | |
| 6,436,098 B1 | 8/2002 | Michelson | |
| 6,447,544 B1 | 9/2002 | Michelson | |
| 6,447,547 B1 | 9/2002 | Michelson | |
| 6,478,823 B1 | 11/2002 | Michelson | |
| 6,540,747 B1 | 4/2003 | Marino | |
| 6,582,432 B1 | 6/2003 | Michelson | |
| 6,605,089 B1 | 8/2003 | Michelson | |
| 6,648,893 B2 | 11/2003 | Dudasik | |
| 6,733,535 B2 | 5/2004 | Michelson | |
| 6,758,849 B1 | 7/2004 | Michelson | |
| 6,770,074 B2 | 8/2004 | Michelson | |
| 6,783,547 B2 | 8/2004 | Castro | |
| 6,875,213 B2 | 4/2005 | Michelson | |
| 6,923,810 B1 | 8/2005 | Michelson | |
| 7,056,321 B2 | 6/2006 | Pagliuca et al. | |
| 7,066,961 B2 | 6/2006 | Michelson | |
| 7,101,398 B2 | 9/2006 | Dooris et al. | |
| 7,115,128 B2 | 10/2006 | Michelson | |
| 7,207,991 B2 | 4/2007 | Michelson | |
| 7,223,269 B2 | 5/2007 | Chappuis | |
| 7,264,622 B2 | 9/2007 | Michelson | |
| 7,288,093 B2 | 10/2007 | Michelson | |
| 7,326,214 B2 | 2/2008 | Michelson | |
| 7,452,369 B2 * | 11/2008 | Barry | 606/279 |
| 7,455,672 B2 | 11/2008 | Michelson | |
| 7,503,933 B2 | 3/2009 | Michelson | |
| 7,517,358 B2 | 4/2009 | Petersen | |
| D597,669 S | 8/2009 | Petersen | |
| 7,674,296 B2 * | 3/2010 | Rhoda et al. | 623/17.15 |
| 7,691,148 B2 * | 4/2010 | Michelson | 623/17.16 |
| 7,708,761 B2 * | 5/2010 | Petersen | 606/247 |
| 7,758,648 B2 * | 7/2010 | Castleman et al. | 623/17.16 |
| 7,850,736 B2 * | 12/2010 | Heinz | 623/17.16 |
| 2002/0138144 A1 | 9/2002 | Michelson | |
| 2002/0198532 A1 | 12/2002 | Michelson | |
| 2003/0135279 A1 | 7/2003 | Michelson | |
| 2003/0139816 A1 | 7/2003 | Michelson | |
| 2003/0158553 A1 | 8/2003 | Michelson | |
| 2004/0073217 A1 | 4/2004 | Michelson | |
| 2004/0133277 A1 | 7/2004 | Michelson | |
| 2004/0225360 A1 | 11/2004 | Malone | |
| 2004/0236331 A1 | 11/2004 | Michelson | |
| 2005/0038512 A1 | 2/2005 | Michelson | |
| 2005/0065518 A1 | 3/2005 | Michelson | |
| 2005/0065519 A1 | 3/2005 | Michelson | |
| 2005/0070898 A1 | 3/2005 | Jones | |
| 2005/0149030 A1 | 7/2005 | Serhan et al. | |
| 2005/0149192 A1 * | 7/2005 | Zucherman et al. | 623/17.11 |
| 2005/0165399 A1 | 7/2005 | Michelson | |
| 2005/0165489 A1 | 7/2005 | Michelson | |
| 2006/0004367 A1 | 1/2006 | Alamin et al. | |
| 2006/0036247 A1 | 2/2006 | Michelson | |
| 2006/0036323 A1 | 2/2006 | Carl et al. | |
| 2006/0058793 A1 | 3/2006 | Michelson | |
| 2006/0064099 A1 | 3/2006 | Pavlov et al. | |
| 2006/0084992 A1 | 4/2006 | Michelson | |
| 2006/0111779 A1 | 5/2006 | Petersen | |
| 2006/0111782 A1 | 5/2006 | Petersen | |
| 2006/0142762 A1 | 6/2006 | Michelson | |
| 2006/0184172 A1 | 8/2006 | Michelson | |
| 2006/0190081 A1 | 8/2006 | Kraus et al. | |
| 2006/0200138 A1 | 9/2006 | Michelson | |
| 2006/0200139 A1 | 9/2006 | Michelson | |
| 2006/0200164 A1 | 9/2006 | Michelson | |
| 2006/0235391 A1 | 10/2006 | Sutterlin, III | |
| 2006/0241758 A1 | 10/2006 | Peterman et al. | |
| 2006/0241764 A1 | 10/2006 | Michelson | |
| 2006/0247650 A1 | 11/2006 | Yerby et al. | |
| 2006/0259142 A1 | 11/2006 | Dooris et al. | |
| 2006/0264953 A1 | 11/2006 | Falahee | |
| 2006/0276790 A1 | 12/2006 | Dawson et al. | |
| 2007/0055373 A1 | 3/2007 | Hudgins et al. | |
| 2007/0083265 A1 | 4/2007 | Malone | |
| 2007/0112428 A1 | 5/2007 | Lancial | |
| 2007/0118218 A1 | 5/2007 | Hooper | |
| 2007/0149976 A1 | 6/2007 | Hale et al. | |
| 2008/0255666 A1 * | 10/2008 | Fisher et al. | 623/17.16 |
| 2009/0076551 A1 | 3/2009 | Petersen | |

OTHER PUBLICATIONS

Whalen, Elizabeth, The Society of Cardiovascular and Interventional Radiology: 17th Annual Scientific Meeting, Apr. 1992, Sep. 1992, pp. 639-645, vol. 159.

Guiot, Bernard H. et al., A Minimally Invasive Technique for Decompression of the Lumbar Spine, Spine, 2002, pp. 432-438, vol. 27, No. 4, Lippincott Williams & Wilkins, Inc.

Park, Youn-Kwan et al., Facet Fusion in the Lumbosacral Spine: A 2-Year Follow-Up Study, Neurosurgery, Jul. 2002, pp. 88-96, vol. 51, No. 1.

Kai, Yukihiro et al., Posterior Lumbar Interbody Fusion Using Local Facet Joint Autograft and Pedicle Screw Fixation, Spine, 2003, pp. 41-46, vol. 29, No. 1, Lippincott Williams & Wilkins, Inc.

Powers, Ciaran J. et al., Minimally Invasive Fusion and Fixation Techniques, Neurosurgery Clinics of North America, 2006, pp. 477-489, vol. 17, Elsevier Inc.

* cited by examiner

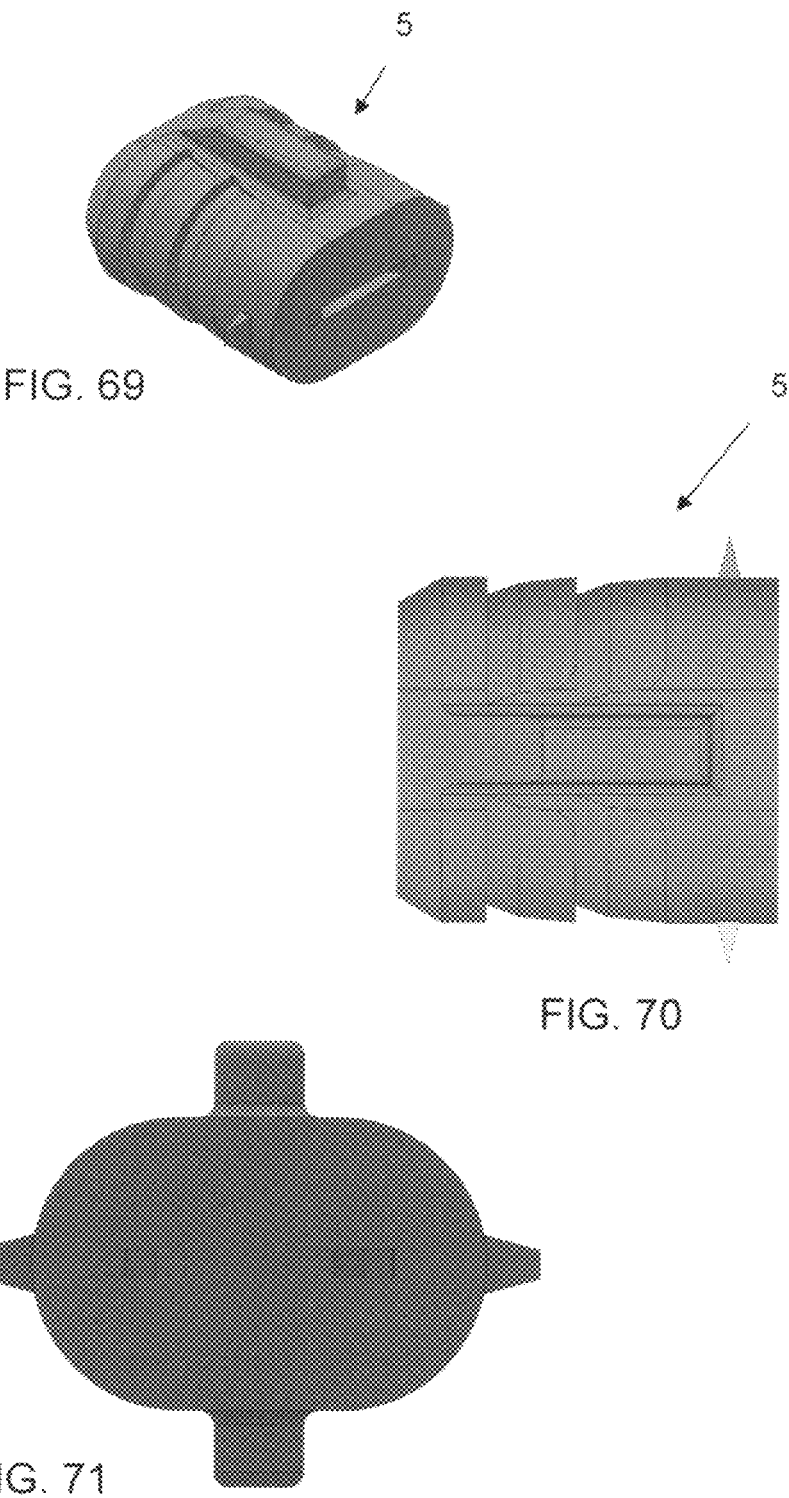

METHOD AND APPARATUS FOR SPINAL FACET FUSION

REFERENCE TO PENDING PRIOR PATENT APPLICATION

This patent application claims benefit of pending prior U.S. Provisional Patent Application Ser. No. 60/939,615, filed May 22, 2007 by Tov Vestgaarden for PERCUTANEOUS SPINAL FACET FIXATION DEVICE FOR FACET FUSION, which patent application is hereby incorporated herein by reference.

FIELD OF THE INVENTION

This invention relates to surgical methods and apparatus in general, and more particularly to surgical methods and apparatus for fusing spinal facets.

BACKGROUND OF THE INVENTION

Disc herniation is a condition where a spinal disc bulges from between two vertebral bodies and impinges on adjacent nerves, thereby causing pain. The current standard of care for surgically treating disc herniation in patients who have chronic pain and who have (or are likely to develop) associated spinal instability is spinal fixation. Spinal fixation procedures are intended to relieve the impingement on the nerves by removing the portion of the disc and/or bone responsible for compressing the neural structures and destabilizing the spine. The excised disc or bone is replaced with one or more intervertebral implants, or spacers, placed between the adjacent vertebral bodies.

In some cases, the spinal fixation leaves the affected spinal segment unstable. In this case, the spinal facets (i.e., the bony fins extending upwardly and downwardly from the rear of each vertebral body) can misengage with one another. The misengagement of the spinal facets can cause substantial pain to the patient. Furthermore, when left untreated, such misengagement of the spinal facets can result in the degeneration of the cartilage located between opposing facet surfaces, ultimately resulting in osteoarthritis, which can in turn lead to worsening pain for the patient.

Thus, where the patient suffers from spinal instability, it can be helpful to stabilize the facet joints as well as the vertebral bodies. The facet joints are frequently stabilized by fusing the spinal facets in position relative to one another.

In addition to providing stability, fusing the spinal facets can also be beneficial in other situations as well. By way of example but not limitation, osteoarthritis (a condition involving the degeneration, or wearing away, of the cartilage at the end of bones) frequently occurs in the facet joints. The prescribed treatment for osteoarthritis disorders depends on the location, severity and duration of the disorder. In some cases, non-operative procedures (including bed rest, medication, lifestyle modifications, exercise, physical therapy, chiropractic care and steroid injections) may be satisfactory treatment. However, in other cases, surgical intervention may be necessary. In cases where surgical intervention is prescribed, spinal facet fusion may be desirable.

A minimally-invasive, percutaneous approach for fusing spinal facets was proposed by Stein et al. ("Stein") in 1993. The Stein approach involved using a conical plug, made from cortical bone and disposed in a hole formed intermediate the spinal facet joint, to facilitate the fusing of opposing facet surfaces. However, the clinical success of this approach was limited. This is believed to be because the Stein approach did not adequately restrict facet motion. In particular, it is believed that movement of Stein's conical plug within its hole permitted unwanted facet movement to occur, thereby undermining facet fusion. Furthermore, the Stein approach also suffered from plug failure and plug migration.

Thus there is a need for a new and improved approach for effecting spinal facet fusion.

SUMMARY OF THE INVENTION

The present invention provides a novel method and apparatus for effecting spinal facet fusion. More particularly, the present invention comprises the provision and use of a novel spinal facet fusion implant for disposition between the opposing articular surfaces of a facet joint, whereby to immobilize the facet joint and facilitate fusion between the opposing facets.

More particularly, in one form of the present invention, there is provided a spinal facet fusion implant comprising:

an elongated body having a distal end, a proximal end and a longitudinal axis extending between the distal end and the proximal end, the elongated body having a cross-sectional profile characterized by a primary axis and a secondary axis; and at least one stabilizer extending radially outwardly from the elongated body in the secondary axis;

wherein the elongated body has a length along the primary axis which is less than the combined width of the spinal facets making up a facet joint;

and further wherein the at least one stabilizer has a width which is sized to make a press fit into the gap between the spinal facets making up a facet joint.

In another form of the present invention, there is provided a method for fusing a spinal facet joint, the method comprising the steps of:

providing a spinal facet fusion implant comprising:
 an elongated body having a distal end, a proximal end and a longitudinal axis extending between the distal end and the proximal end, the elongated body having a cross-sectional profile characterized by a primary axis and a secondary axis; and
 at least one stabilizer extending radially outwardly from the elongated body in the secondary axis;
 wherein the elongated body has a length along the primary axis which is less than the combined width of the spinal facets making up a facet joint;
 and further wherein the at least one stabilizer has a width which is sized to make a press fit into the gap between the spinal facets making up a facet joint;

deploying the spinal facet fusion implant in the facet joint so that the elongated body is simultaneously positioned within both of the facets of the facet joint and the at least one stabilizer is positioned within the gap between the spinal facets; and maintaining the spinal facet fusion implant in this position while fusion occurs.

In another form of the present invention, there is provided a spinal facet fusion implant comprising:

an elongated body having a distal end, a proximal end and a longitudinal axis extending between the distal end and the proximal end, the elongated body having a cross-sectional profile which is characterized by a primary axis and a secondary axis;

wherein the elongated body has a length along the primary axis which is less than the combined width of the spinal facets making up a facet joint;

and further wherein the cross-sectional profile is non-circular.

In yet another form of the present invention, there is provided a method for fusing a spinal facet joint, the method comprising the steps of:

providing a spinal facet fusion implant comprising:
an elongated body having a distal end, a proximal end and a longitudinal axis extending between the distal end and the proximal end, the elongated body having a cross-sectional profile which is characterized by a primary axis and a secondary axis;
wherein the elongated body has a length along the primary axis which is less than the combined width of the spinal facets making up a facet joint;
and further wherein the cross-sectional profile is non-circular;

deploying the spinal facet fusion implant in the facet joint so that the elongated body is simultaneously positioned within both of the facets of the facet joint; and maintaining the spinal facet fusion implant in this position while fusion occurs.

In still another form of the present invention, there is provided a joint fusion implant comprising:

an elongated body having a distal end, a proximal end and a longitudinal axis extending between the distal end and the proximal end, the elongated body having a cross-sectional profile characterized by a primary axis and a secondary axis; and at least one stabilizer extending radially outwardly from the elongated body in the secondary axis;

wherein the elongated body has a length along the primary axis which is less than the combined width of the bones making up the joint;

and further wherein the at least one stabilizer has a width which is sized to make a press fit into the gap between the bones making up the joint.

In an additional form of the present invention, there is provided a method for fusing a joint, the method comprising the steps of:

providing a fusion implant comprising:
an elongated body having a distal end, a proximal end and a longitudinal axis extending between the distal end and the proximal end, the elongated body having a cross-sectional profile characterized by a primary axis and a secondary axis; and
at least one stabilizer extending radially outwardly from the elongated body in the secondary axis;
wherein the elongated body has a length along the primary axis which is less than the combined width of the bones making up the joint;
and further wherein the at least one stabilizer has a width which is sized to make a press fit into the gap between the bones making up the joint;

deploying the fusion implant in the joint so that the elongated body is simultaneously positioned within both of the bones of the joint and the at least one stabilizer is positioned within the gap between the bones; and maintaining the fusion implant in this position while fusion occurs.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 29-74 illustrate alternative fusion implants formed in accordance with the present invention.

DETAILED DESCRIPTION OF THE INVENTION

In General

Figure 1:
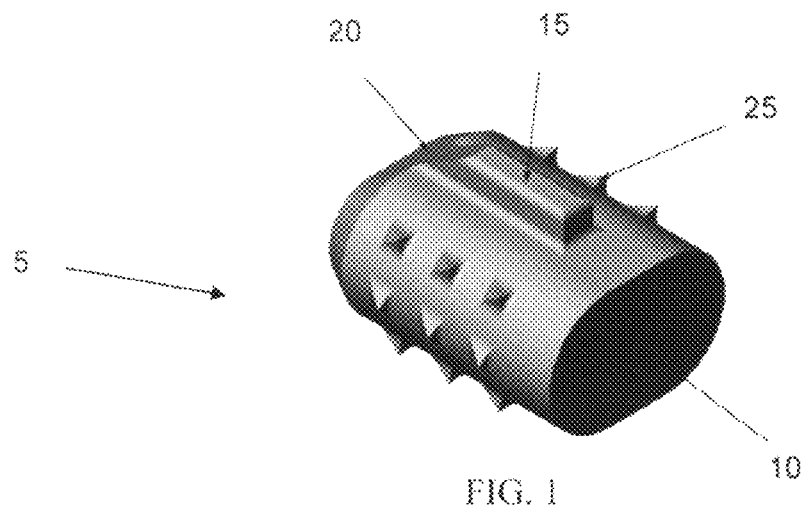
FIGS. 1-3 illustrate fusion implants formed in accordance with the present invention.

Looking first at FIG. 1, there is shown a novel spinal facet fusion implant 5 formed in accordance with the present invention. Fusion implant 5 generally comprises a body 10 and at least one stabilizer 15.

Body 10 comprises an elongated element having structural integrity. Preferably the distal end of body 10 (and the distal end of stabilizer 15 as well) is chamfered as shown at 20 to facilitate insertion of fusion implant 5 into the facet joint, as will hereinafter be discussed. Preferably, and as seen in FIG. 1, body 10 has a rounded rectangular cross-section, or an ovoid cross-section, a laterally-extended cross-section, or some other non-round cross-section, so as to inhibit rotation of body 10 about a longitudinal center axis. If desired, body 10 may include a plurality of barbs (i.e., forward biting teeth) 25 extending outwardly therefrom. Barbs 25 are designed to permit body 10 to be inserted into the facet joint and to impede retraction of body 10 out of the facet joint.

The at least one stabilizer 15 is intended to be received in the gap located between the opposing facet surfaces, whereby to prevent rotation of fusion implant 5 within the facet joint. In one preferred form of the present invention, two stabilizers 15 are provided, one disposed along the upper surface of body 10 and one disposed along the lower surface of body 10. Stabilizers 15 preferably have a width just slightly larger than the gap between the opposing articular surfaces of a facet joint, so that the stabilizers can make a snug fit therebetween.

Figure 2:
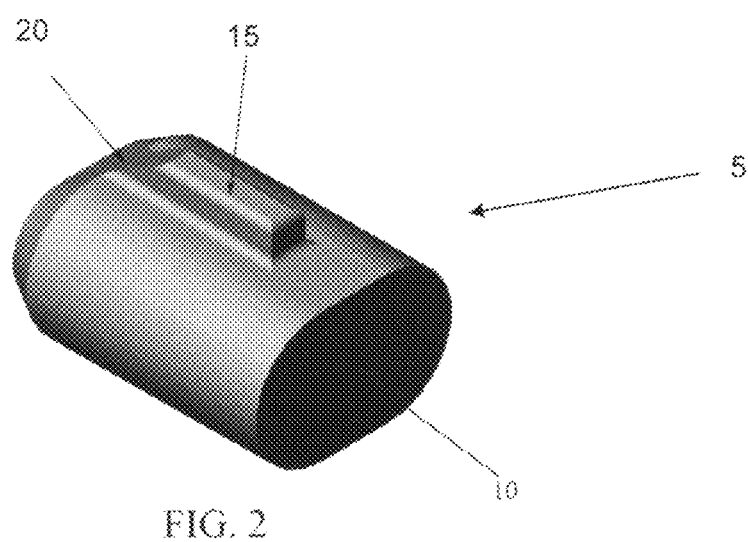

If desired, and looking now at FIG. 2, fusion implant 5 may also be configured so that its body 10 lacks barbs 25 on its outer surface.

Figure 3:
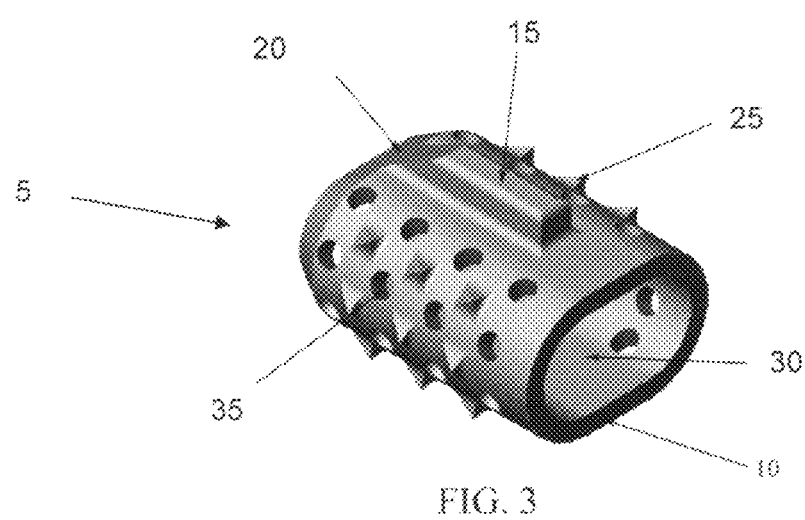

Alternatively, if desired, and looking now at FIG. 3, fusion implant 5 may comprise a hollow body 10 having an internal cavity 30. Hollow body 10 may also have a plurality of openings 35 extending through the side wall of body 10 and communicating with cavity 30. Internal cavity 30 and openings 35 can facilitate facet fusion by permitting bone ingrowth into and/or through fusion implant 5.

Fusion implant 5 is intended to be inserted into a facet joint using a posterior approach. The posterior approach is familiar to spine surgeons, thereby providing an increased level of comfort for the surgeon, and also minimizing the possibility of damage to the spinal cord during fusion implant insertion.

Figure 4:
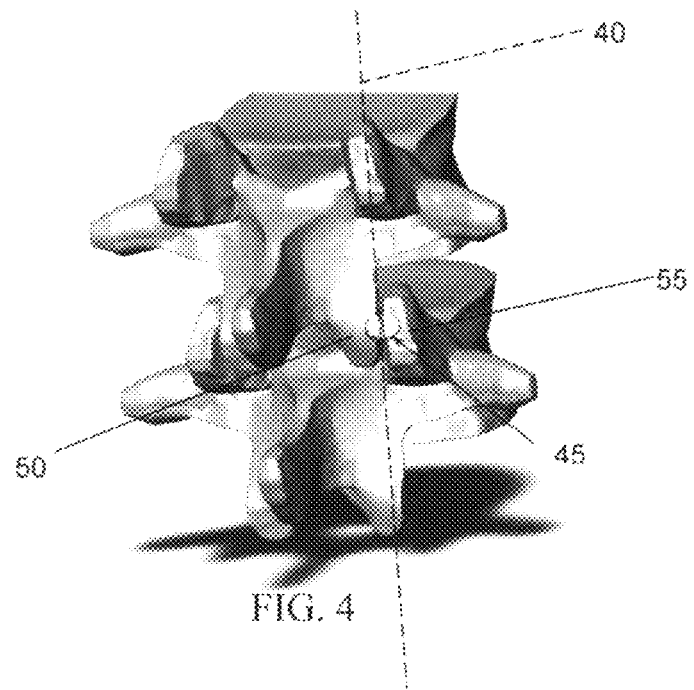
FIGS. 4 and 5 illustrate a fusion implant being installed in a facet joint.

In use, and looking now at FIG. 4, an instrument is first used to determine the vertical plane 40 of the facet joint. Identifying the vertical plane of the facet joint is important, since this is used to identify the proper position for a cavity 45 which is to be formed in the facet joint to receive the fusion implant.

To this respect it should be appreciated that at least one of the instruments comprises a directional feature which is used to maintain the alignment of the instrumentation with the vertical plane of the facet joint. By way of example but not limitation, a directional cannula may comprise a flat portion and the remaining instruments may comprise a flat portion on an opposite portion of the instrument so that the instruments may only be inserted through the cannula at 0 degrees and/or 180 degrees.

After the proper position for cavity 45 has been identified, a drill (or reamer, punch, dremel, router, burr, etc.) is used to form the cavity 45 in the facet joint. Cavity 45 is formed across vertical plane 40 so that substantially one-half of cavity 45 is formed in a first facet 50, and substantially one-half is formed in its opposing facet 55.

Figure 5:
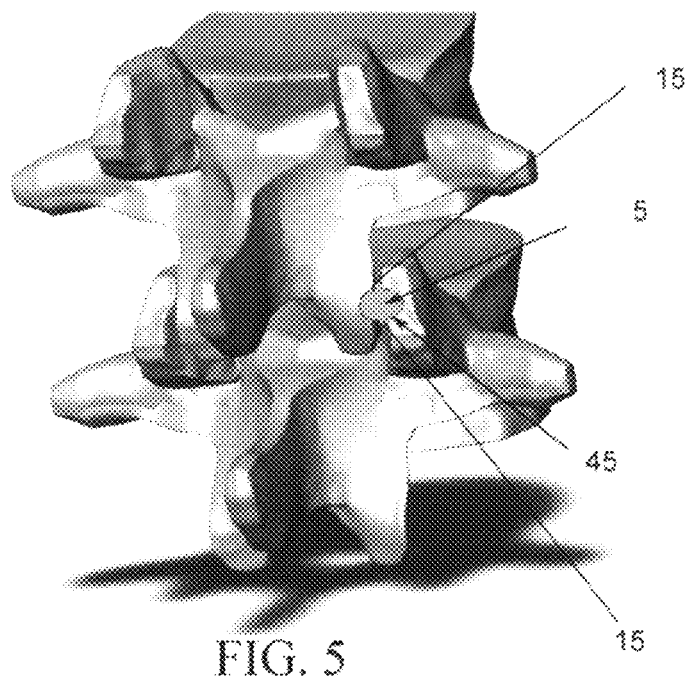

After cavity 45 has been formed in (or, perhaps more literally, across) the facet joint, fusion implant 5 is inserted into cavity 45. See FIG. 5. More particularly, fusion implant 5 is inserted into cavity 45 so that (i) body 10 spans the gap between opposing facets 50, 55, and (ii) stabilizers 15 extend between the opposing facet surfaces. Preferably, fusion implant 5 is slightly oversized relative to cavity 45 so as to create a press fit. Fusion implant 5 provides the stability and strength needed to immobilize the facet joint while fusion occurs. Due to the positioning of stabilizers 15 between the opposing facet surfaces, and due to the non-circular cross-section of body 10, fusion implant 5 will be held against rotation within cavity 45, which will in turn hold facets 50, 55 stable relative to one another.

It should be appreciated that where the hollow fusion implant 10 of FIG. 3 is used, and where the implant is formed out of a sufficiently strong and rigid material, cavity 45 need not be pre-formed in the opposing facets. In this case, the hollow fusion implant can be simply tapped into place, in much the same manner that a punch is used.

Thus it will be seen that the present invention provides a new and improved fusion implant for facilitating facet fusion. This new fusion implant is able to withstand greater forces, prohibit motion in all directions and drastically reduce the risk of implant failure. The new fusion implant also eliminates the possibility of slippage during spinal motion, greatly improves facet stability and promotes better facet fusion.

It should be appreciated that the new fusion implant combines two unique "shapes" in one implant (i.e., the shape of body 10 and the shape of stabilizer 15) in order to limit motion in a multi-directional joint. More particularly, the shape of body 10 limits motion (e.g., in flexion/extension for the lumbar facets and in axial rotation for the cervical facets), while the shape of stabilizer 15 (i.e., the "keel") rests between two bony structures (i.e., in the gap of the facet joint) and limits lateral bending. This construction eliminates the possibility of eccentric forces inducing motion in the facet joint.

Furthermore, it has been found that while the present invention effectively stabilizes the joint, it still allows the "micro motion" which is required for the fusion process to begin.

It should be appreciated that the new fusion implant may be manufactured in a wide range of different sizes in order to accommodate any size of facet joint. Furthermore, the scale and aspect ratio of body 10, stabilizers 15, barbs 25, openings 35, etc. may all be varied without departing from the scope of the present invention. Additionally, the new fusion implant may be constructed out of any substantially biocompatible material which has properties consistent with the present invention including, but not limited to, allograft, autograft, synthetic bone, simulated bone material, biocomposites, ceramics, PEEK, stainless steel and titanium. Thus, the present invention permits the surgeon to select a fusion implant having the appropriate size and composition for a given facet fusion.

Detailed Surgical Technique

Solid Fusion Implant

Figure 6:
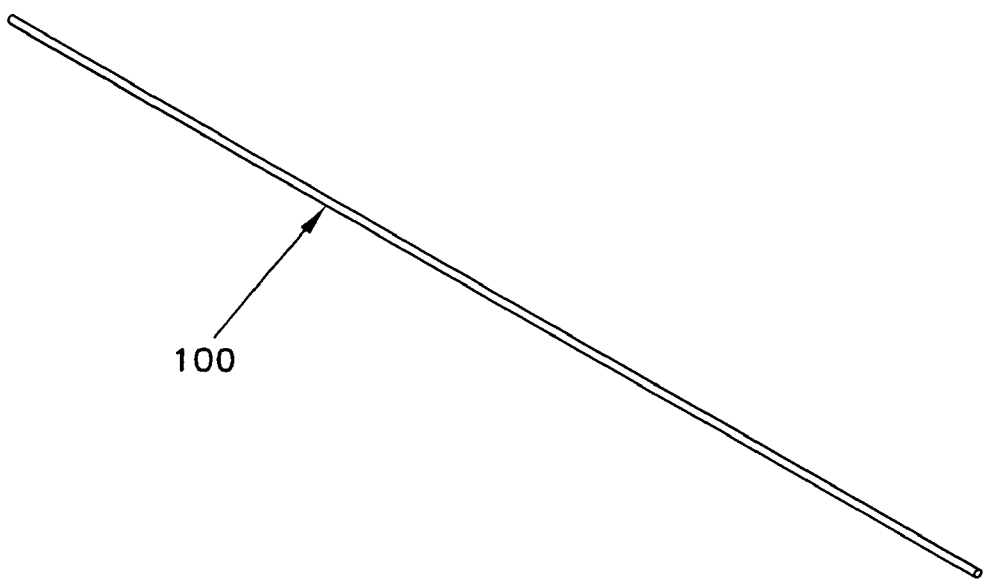
FIGS. 6-12 illustrate instrumentation which may be used to install a solid fusion implant in a facet joint.
Figure 7:
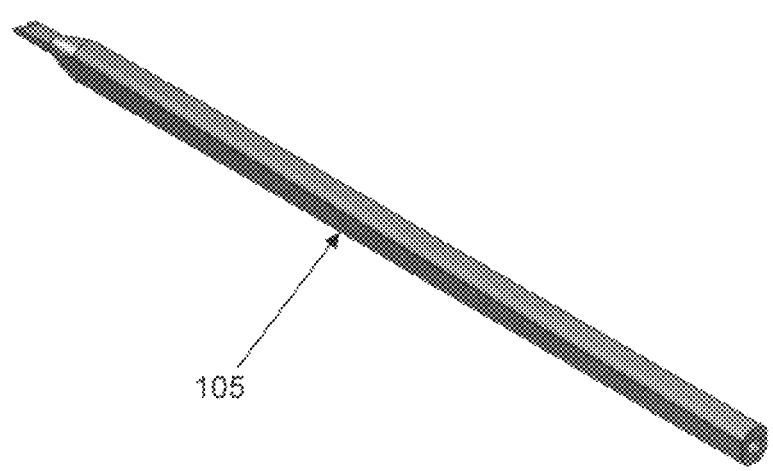
Figure 8:
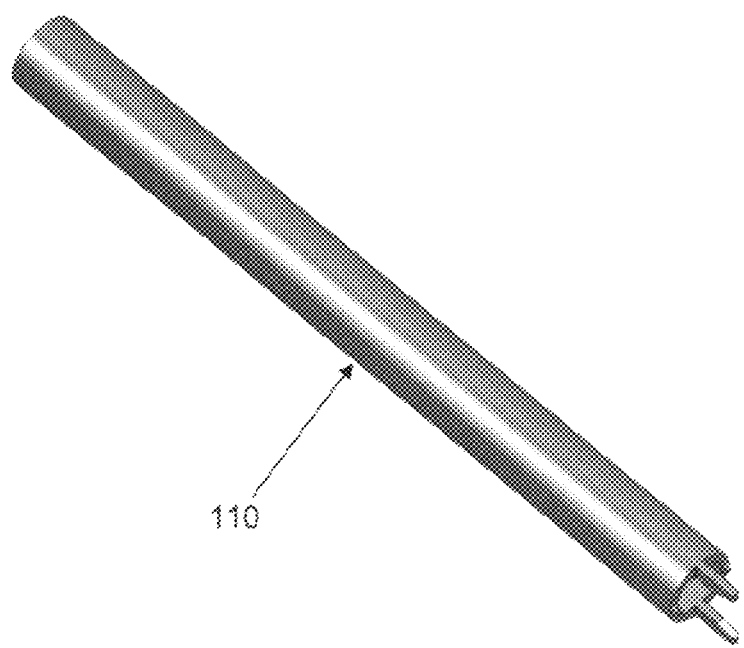
Figure 9:
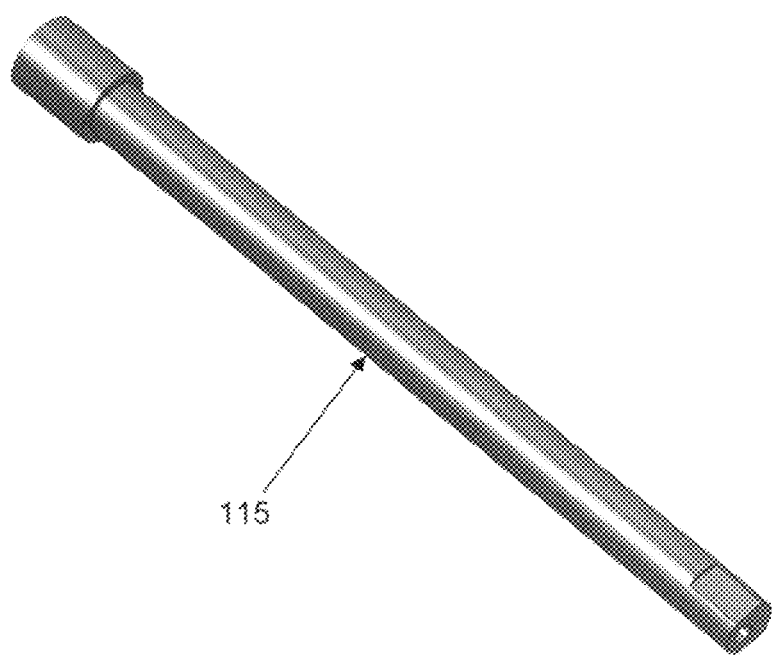
Figure 9A:
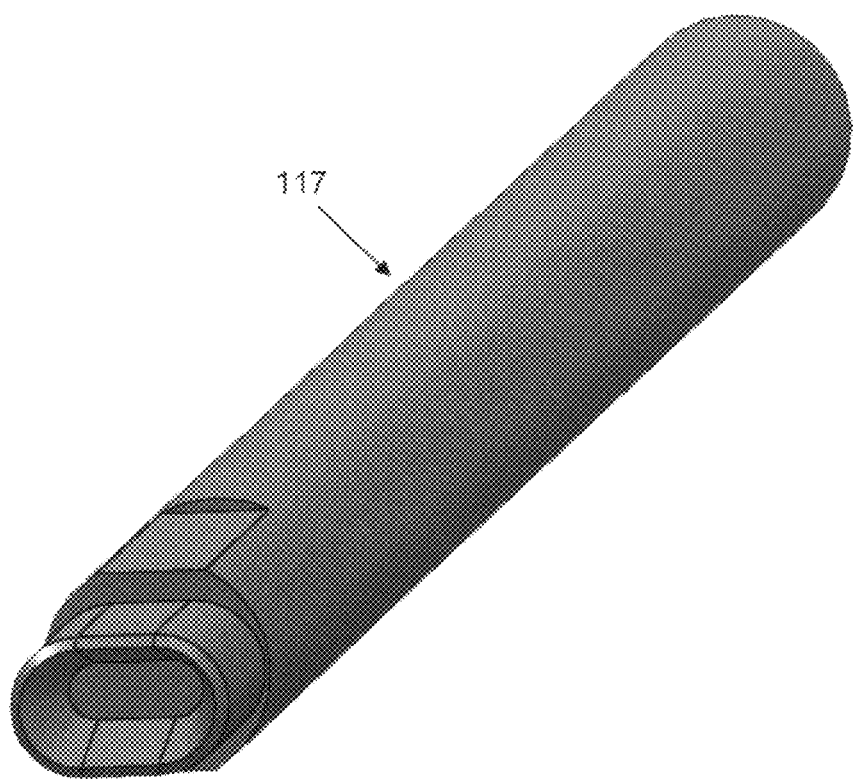
Figure 11:
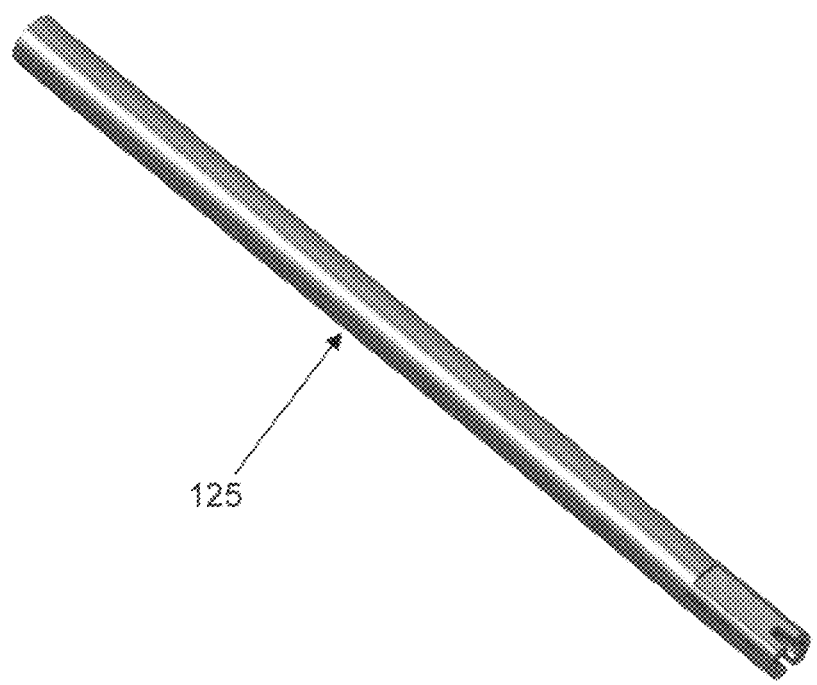
Figure 12:
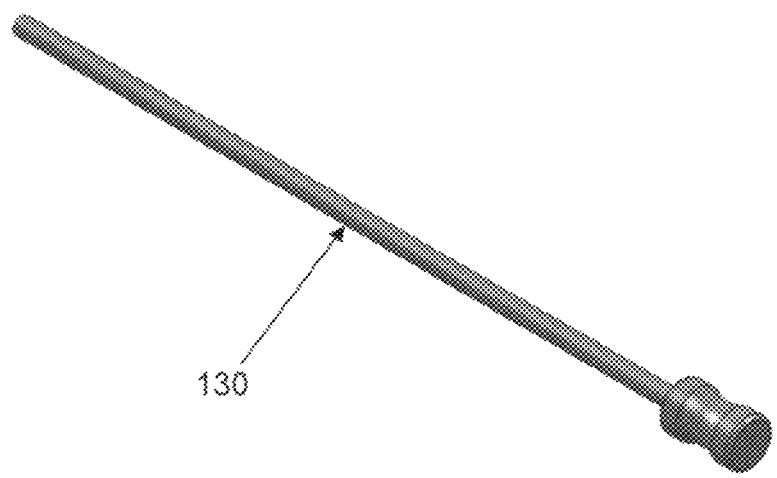

A preferred surgical technique for utilizing a solid fusion implant 5 will now be described. The preferred surgical technique preferably uses a guide pin 100 (FIG. 6) a facet distractor 105 (FIG. 7), a directional cannula 110 (FIG. 8), a drill guide 115 (FIG. 9), a cavity cutter 117 (FIG. 9A), an implant loading block 120 (FIG. 10), an implant holder 125 (FIG. 11) and an implant tamp 130 (FIG. 12).

Figure 13:
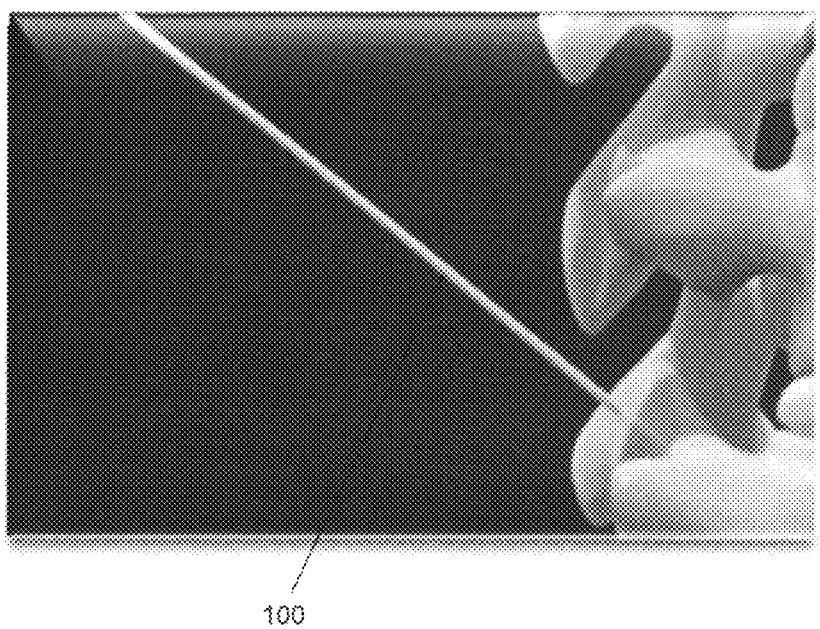
FIGS. 13-26 illustrate a preferred method for installing a solid fusion implant in the facet joint.

First, the facet joint is localized indirectly by fluoroscopy, or directly by visualization during an open procedure. Next, a guide pin 100 (FIG. 13) is inserted into the gap between the opposing facet surfaces. The position of guide pin 100 is verified by viewing the coronal and sagittal planes. Then guide pin 100 is lightly tapped so as to insert the guide pin approximately 5 mm into the facet joint, along vertical plane 40. In this respect it will be appreciated that the inferior facet is curved medially and will help prevent the guide pin from damaging the nerve structures.

Figure 14:
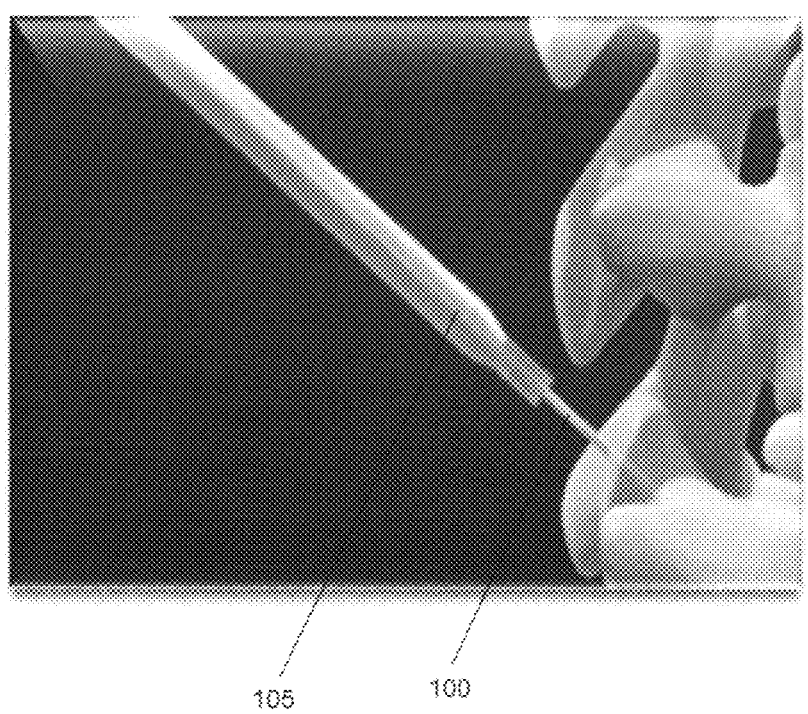
Figure 15:
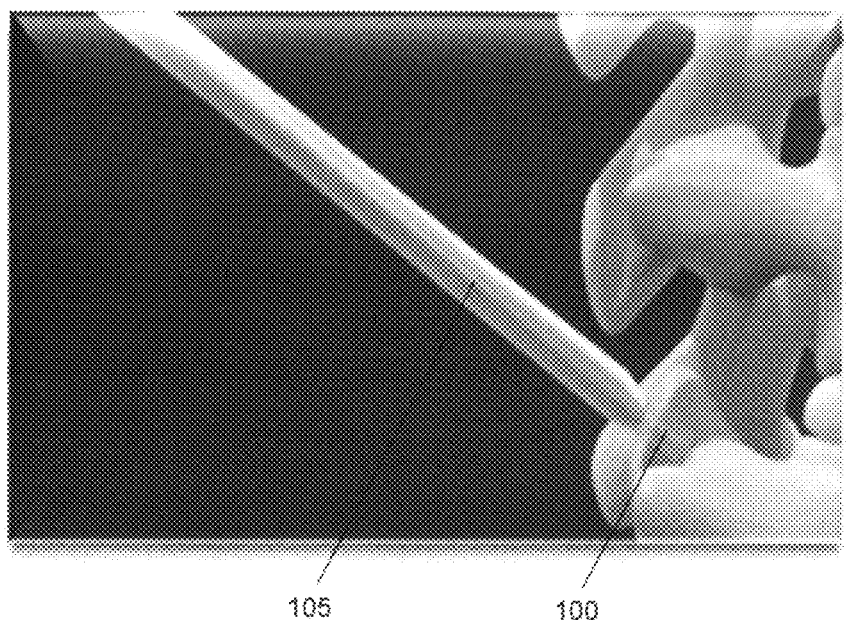

Next, a cannulated facet distractor 105 is slid over guide pin 100 (FIG. 14) so that it is aligned with the vertical plane of the facet joint. Then facet distractor 105 is lightly tapped into the facet joint, along vertical plane 40 (FIG. 15).

Figure 16:
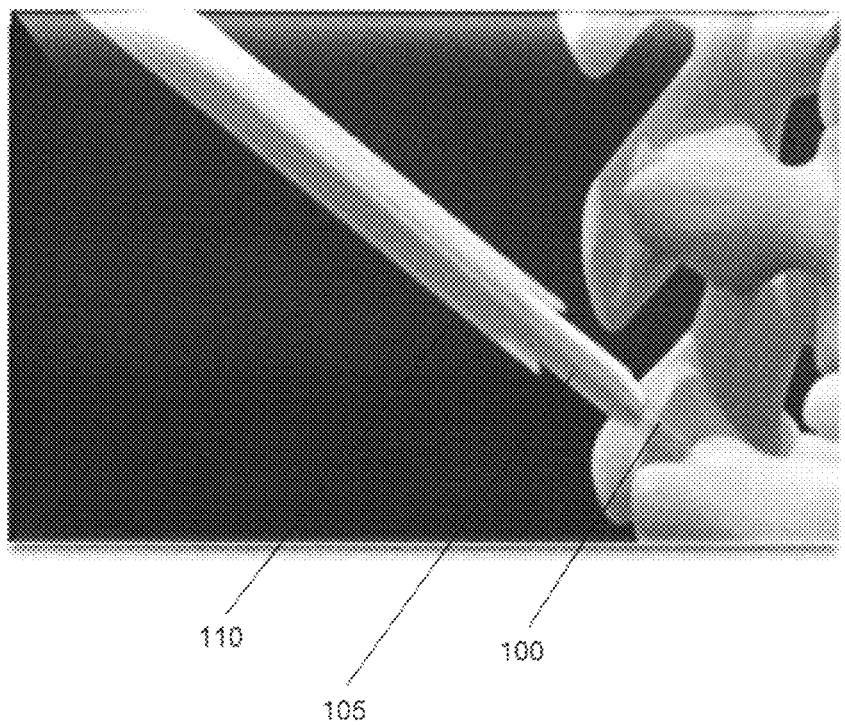
Figure 17:
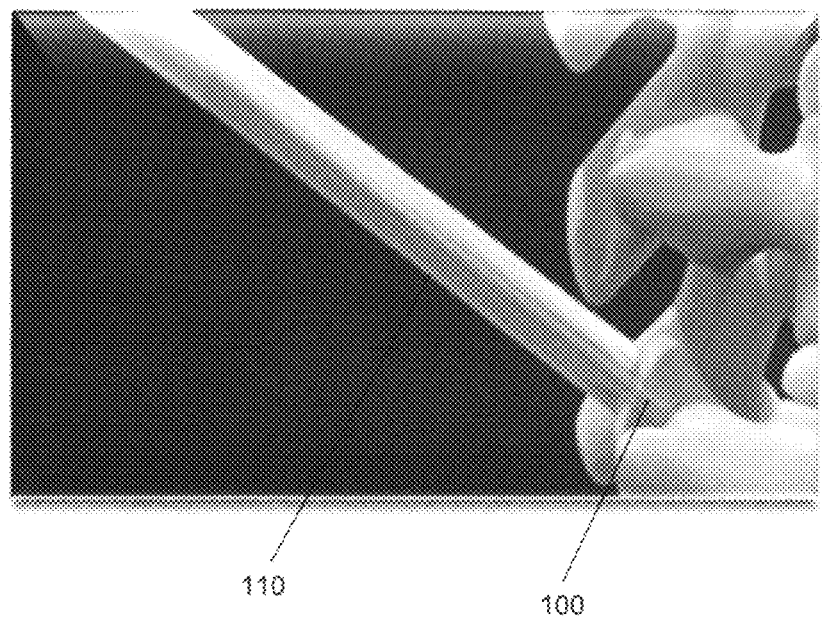
Figure 18:
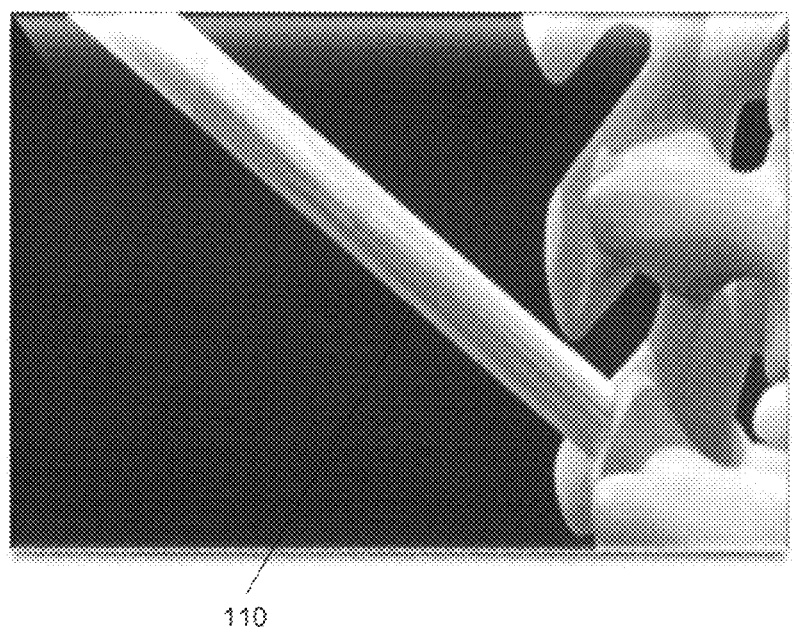

Next, a directional cannula 110 is placed over facet distractor 105 (FIG. 16). Then the tip of directional cannula 110 is pushed into the facet joint (FIG. 17). Once the tip of directional cannula 110 has entered the facet joint, the directional cannula is lightly tapped so as to seat the cannula in the facet joint. This aligns directional cannula 110 with the vertical plane of the facet joint. After verifying that directional cannula 110 has been inserted all the way into the facet joint and is stabilized in the joint, facet distractor 105 is removed (FIG. 18).

Figure 19:
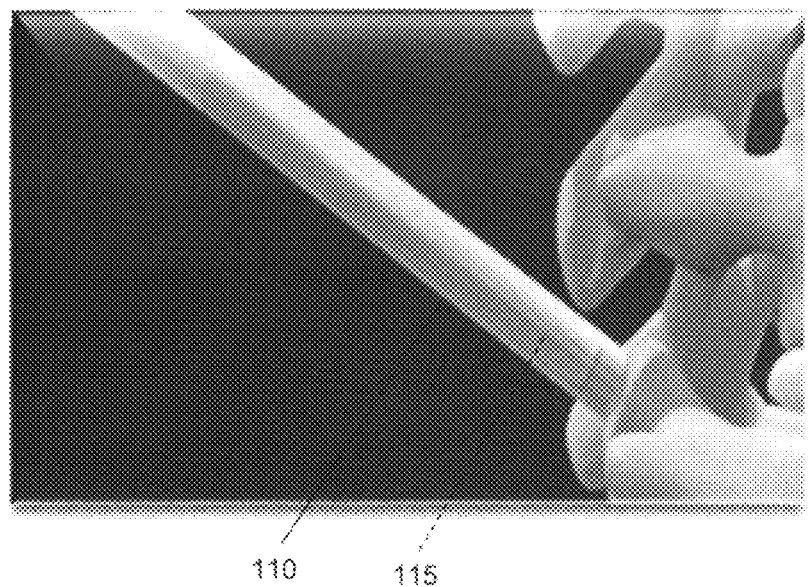
Figure 20:
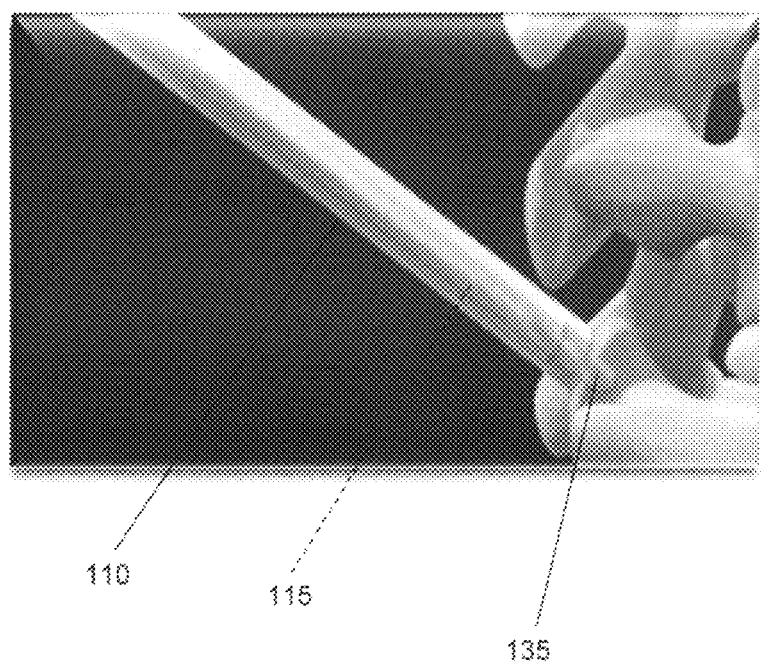
Figure 21:
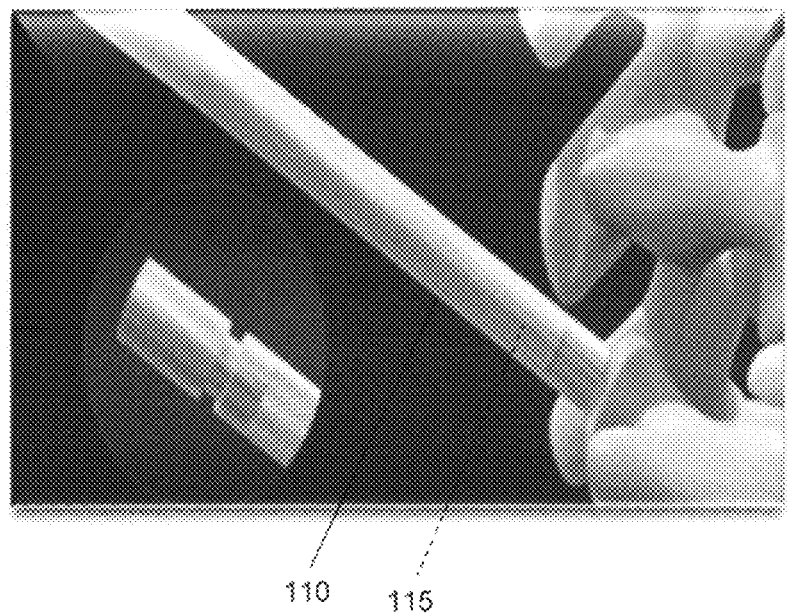
Figure 22:
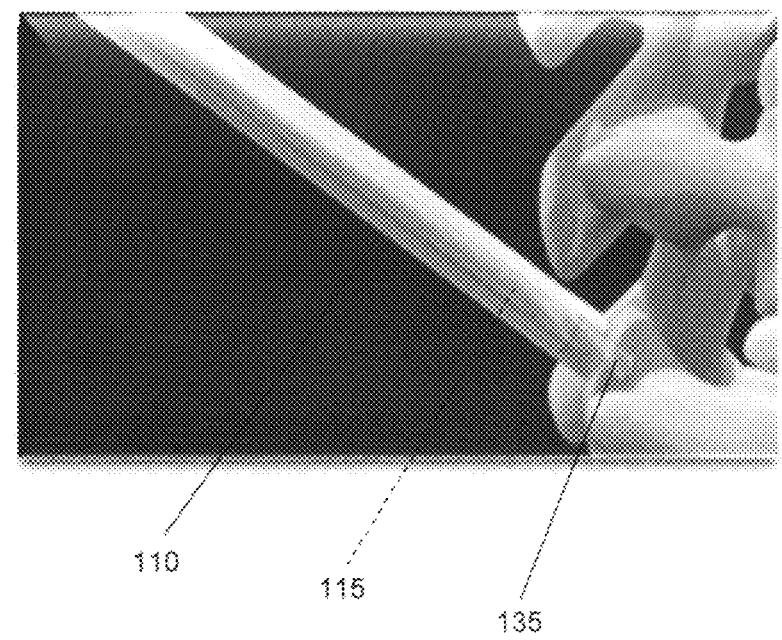
Figure 23:
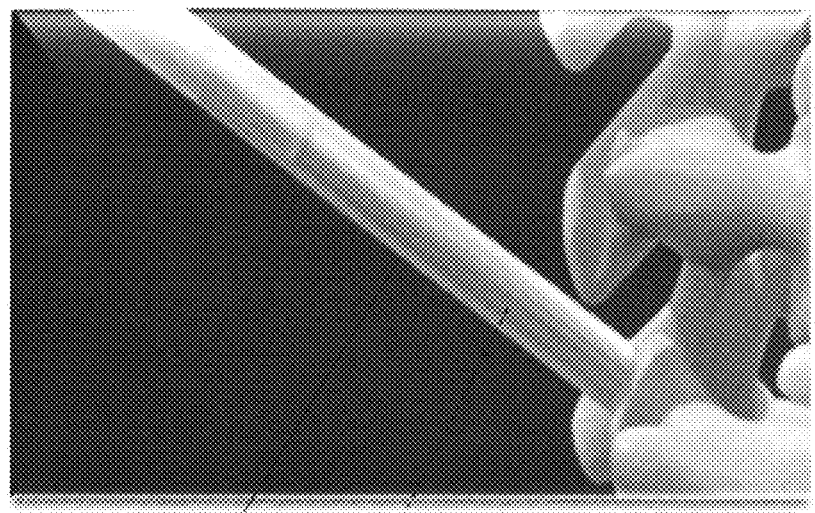

Next, a drill guide 115 is inserted into directional cannula 110 (FIG. 19). Drill guide 115 is advanced within directional cannula 110 until a drill guide stop is resting on directional cannula 110. Then, with drill guide 115 in place, irrigation (e.g., a few drops of saline) is placed into drill guide. Next, a drill bit 135 is used to drill a cavity in the inferior facet (FIG. 20). This is done by drilling until drill bit 135 reaches the mechanical stop on drill guide 115 (FIG. 21). Then drill guide 115 and drill bit 135 are pulled out of directional cannula 110, drill guide 115 is rotated 180 degrees, and then drill guide 115 is reinserted into directional cannula 110 in order to drill the superior facet. With drill guide 115 in place, irrigation (e.g., a few drops of saline) is placed into drill guide 115, and then drill bit 135 is used to drill a cavity in the superior facet (FIG. 22). Again, drilling occurs until drill bit 135 reaches the mechanical stop on drill guide 115. Then drill bit 135 is removed (FIG. 23).

A cavity cutter 117 is then used to make an opening having the perfect shape for fusion implant 5.

Figure 10:
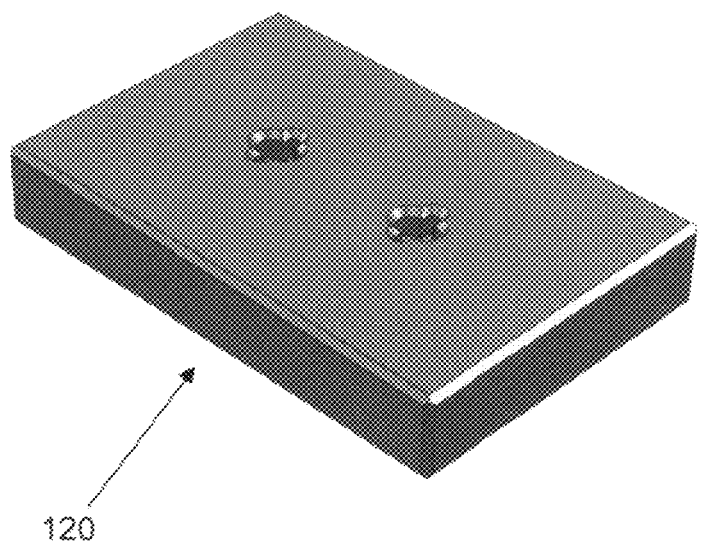
Figure 24:
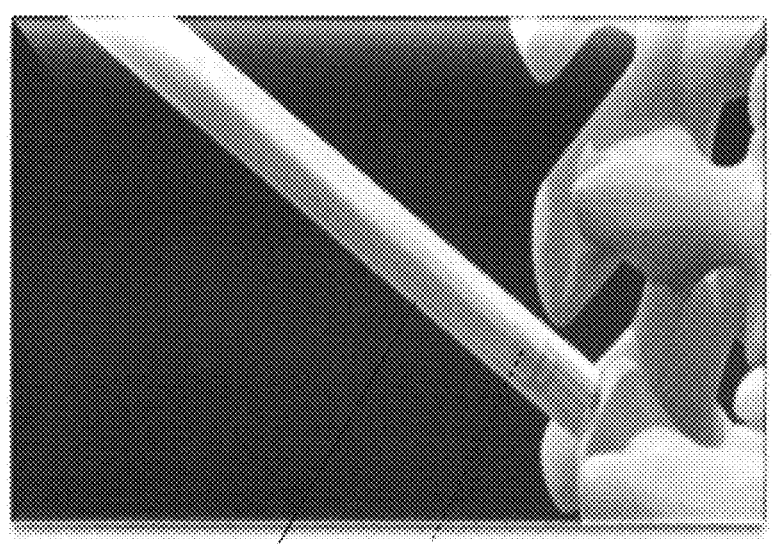
Figure 25:
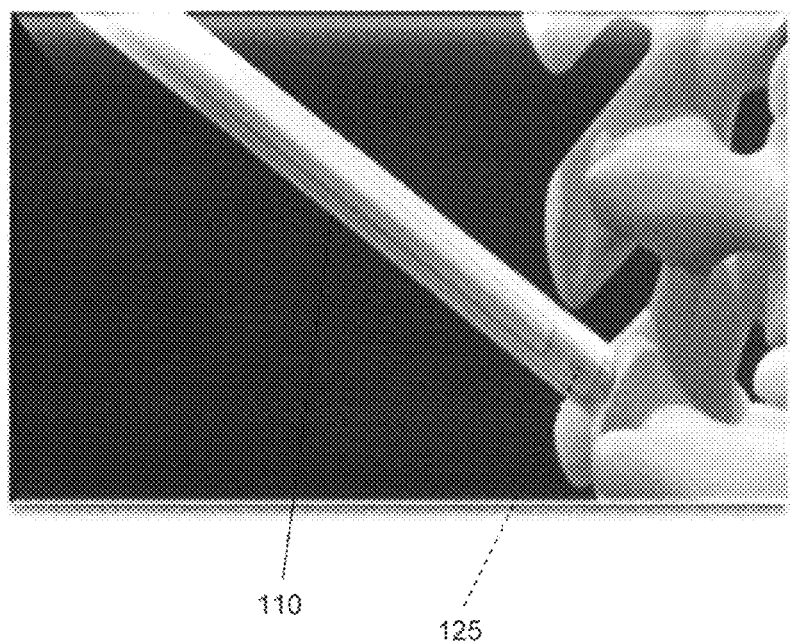
Figure 26:
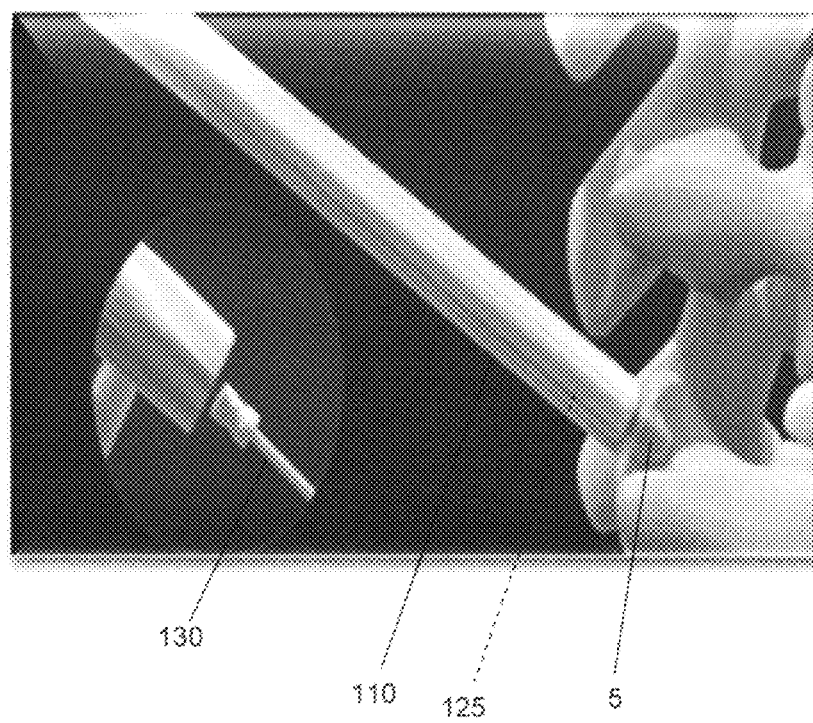

Using implant loading block 120 shown in FIG. 10, fusion implant 5 is then inserted into implant holder 125. Then implant holder 125, with fusion implant 5 in place, is placed into directional cannula 110 (FIG. 24). Next, implant holder 125 is lightly tapped so as to insert fusion implant 5 into the cavity created in the facet joint (FIG. 25). Once the implant has been positioned in the cavity created in the facet joint, implant tamp 130 is inserted into implant holder 125. Next, implant tamp 130 is lightly tapped so as to drive the implant into the cavity created in the facet joint (FIG. 26). The implant is preferably countersunk 1-2 mm into the facet joint.

Then the foregoing steps are repeated for the contralateral facet joint.

Finally, implant tamp 130, implant holder 125 and directional cannula 110 are removed from the surgical site and the incision is closed.

Detailed Surgical Technique

Hollow Fusion Implant

Figure 27:
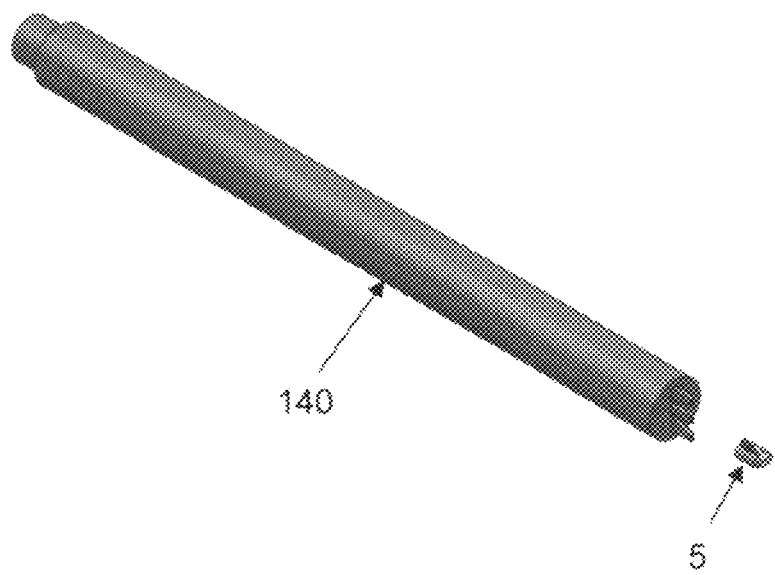
FIGS. 27-28 illustrate instrumentation which may be used to install a hollow fusion implant in a facet joint.

A preferred surgical technique for utilizing a hollow fusion implant 5 will now be described. The preferred surgical technique preferably uses guide pin 100 (FIG. 6), facet distractor 105 (FIG. 7), and an implant punch 140 (FIG. 27).

First, the facet joint is localized indirectly by fluoroscopy or directly by visualization during an open procedure. Next, guide pin 100 is inserted in the gap between the opposing facet surfaces. The position of guide pin 100 is verified by viewing the coronal and sagittal planes. Then guide pin 100 is lightly tapped so as to insert guide pin 100 approximately 5 mm into the facet joint, along the vertical plane of the facet joint. In this respect it will be appreciated that inasmuch as the inferior facet curves medially, this will help prevent the guide pin from damaging the nerve structures.

Then the cannulated facet distractor 105 is slid over guide pin 100 so that it is aligned with the vertical plane of the facet joint. Facet distractor 105 is lightly tapped into the facet joint, along the vertical plane of the facet joint.

Figure 28:
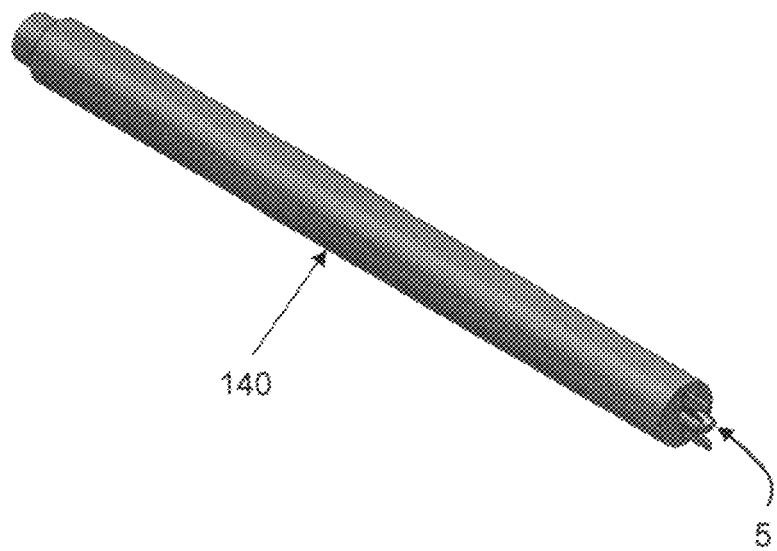

Next, implant punch 140 (FIG. 27), with a hollow fusion implant 5 mounted thereto (FIG. 28) is pushed (or hammered or otherwise advanced) downwards so as to drive hollow fusion implant 5 into the facet joint.

Finally, implant punch 140 and guide pin 100 are removed, leaving hollow fusion implant 5 in the facet joint, and the incision is closed.

Alternative Constructions

The configuration of fusion implant 5 may be varied without departing from the scope of the present invention.

Figure 29:
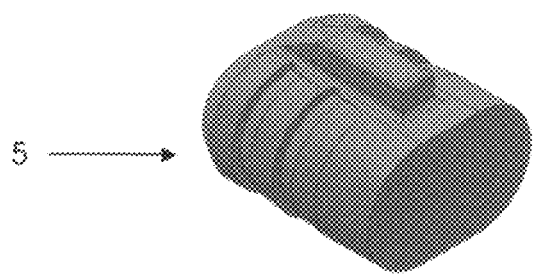
Figure 30:
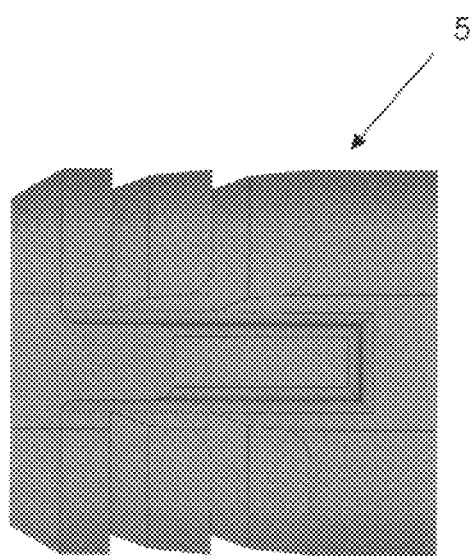
Figure 31:
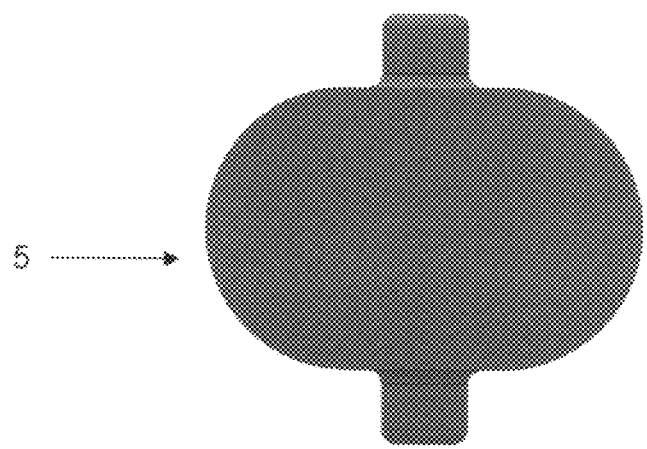

In one configuration, and looking now at FIGS. 29-31, there is provided a fusion implant 5 comprising a rounded rectangular elongated body and two stabilizers. Preferably, the body comprises a groove extending circumferentially around the exterior surface of the body.

Figure 32:
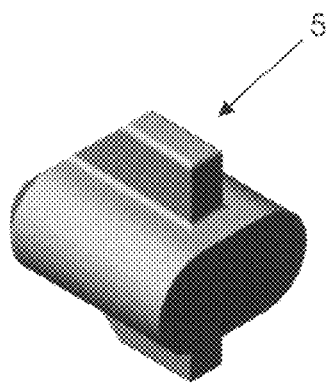
Figure 33:
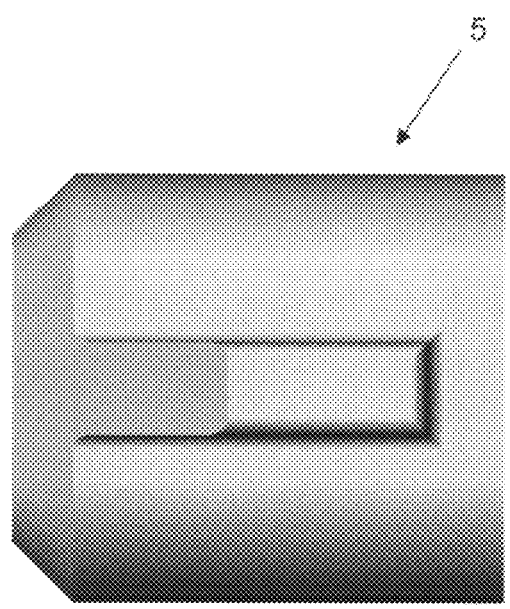
Figure 34:
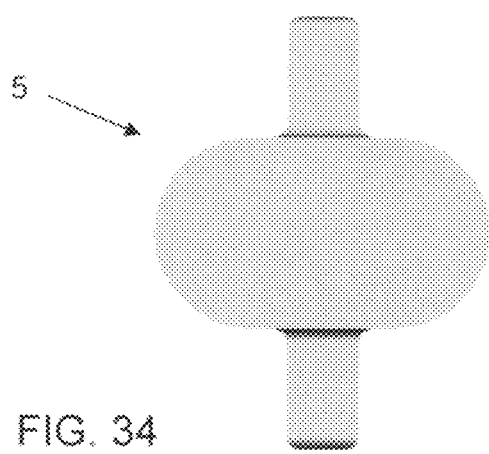

Looking next at FIGS. 32-34, there is shown a fusion implant 5 comprising a rounded elongated body, which is similar to the embodiment shown in FIGS. 29-31, however, the elongated body has a different aspect ratio and the elongated body is formed with a substantially smooth outer surface (e.g., without grooves or barbs).

Figure 35:
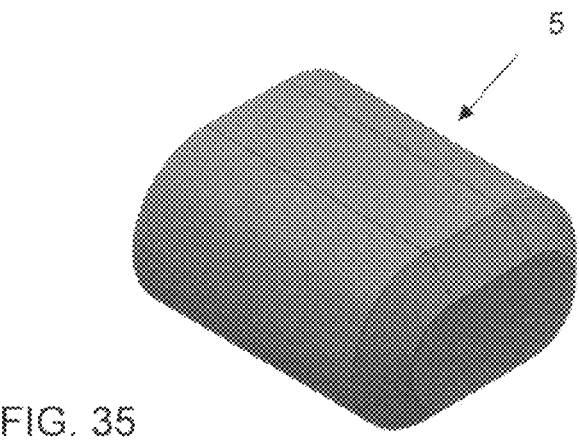
Figure 36:
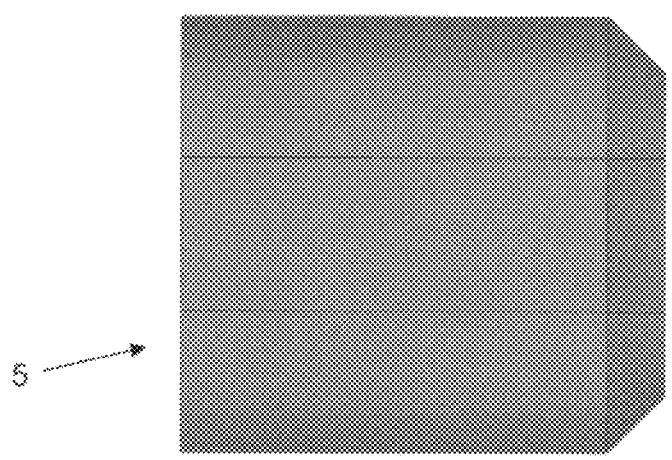
Figure 37:
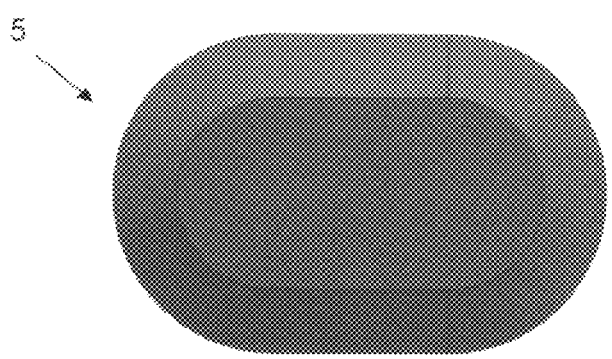

FIGS. 35-37 illustrate a fusion implant 5 having an elongated body which is similar to the elongated body shown in FIGS. 29-31, but without a stabilizer and with an elongated body which is formed with a substantially smooth outer surface (e.g., without grooves or barbs).

Figure 38:
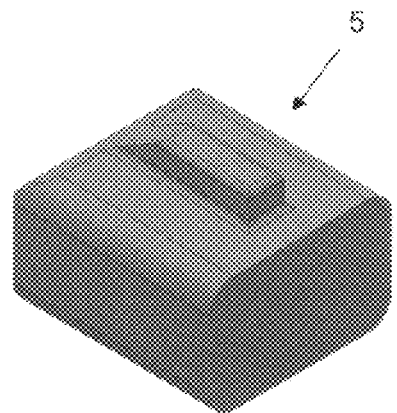
Figure 39:
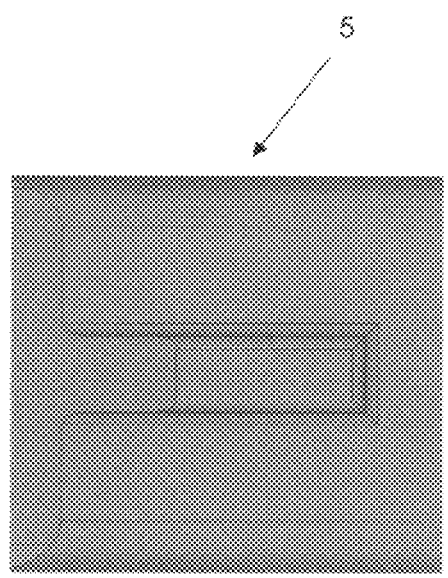
Figure 40:
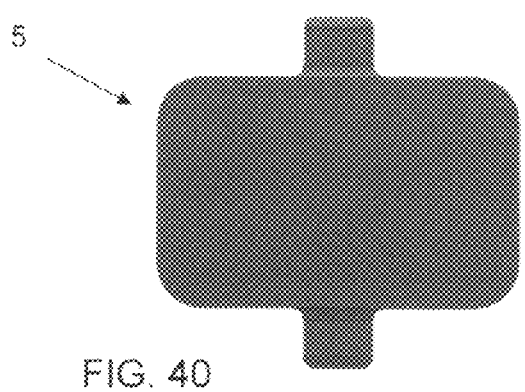

FIGS. 38-40 illustrate a fusion implant 5 having an elongated body with a smaller radius on the rounded edges than the embodiment shown in FIGS. 29-31. Furthermore, the elongated body is formed with a smooth outer surface.

Figure 41:
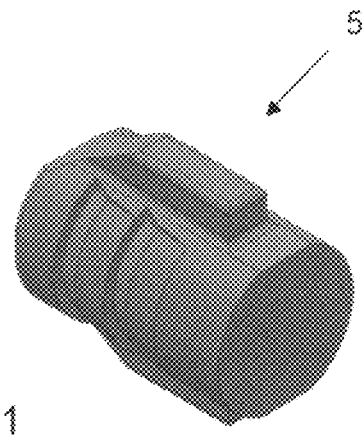
Figure 42:
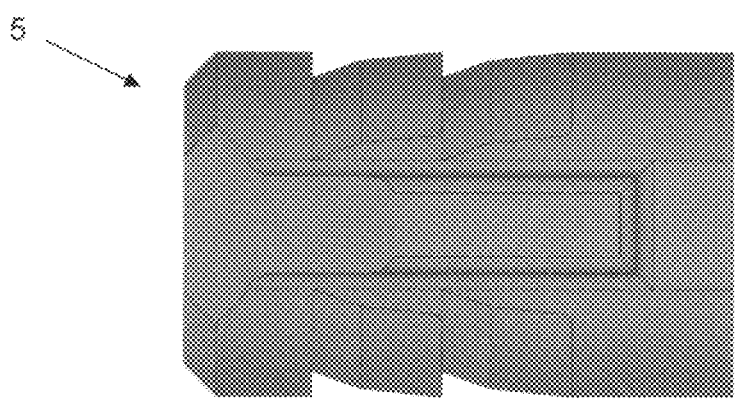
Figure 43:
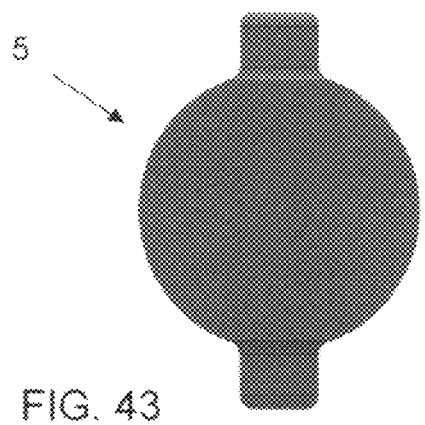
Figure 44:
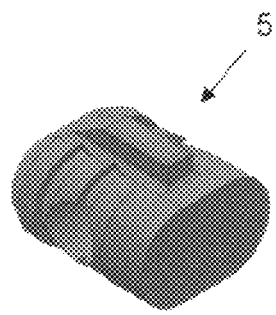
Figure 45:
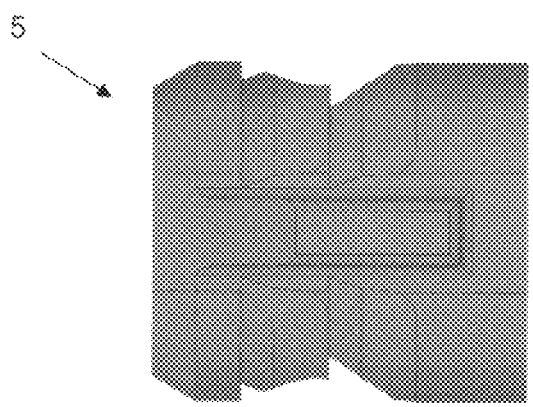
Figure 46:
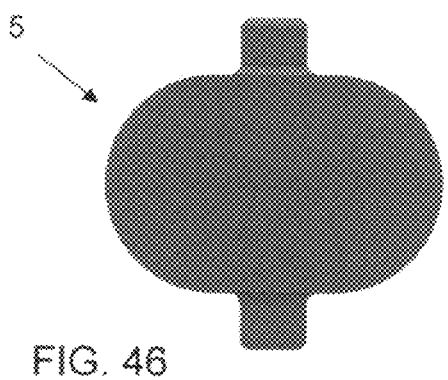
Figure 47:
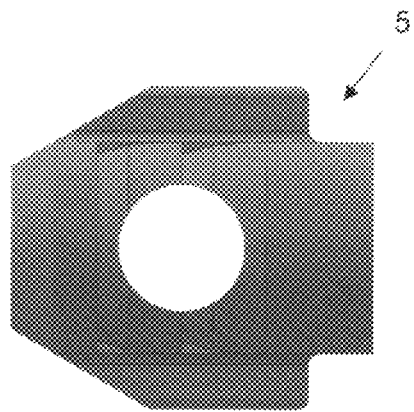

FIGS. 41-43 illustrate a fusion implant 5 which is similar to the implant of FIGS. 29-31, but with the main body having a substantially circular configuration.

FIGS. 44-47 illustrate a fusion implant 5 which is similar to the implant of FIGS. 29-31 and further comprises a through-hole extending through the elongated body. The through-hole allows a bone growth promoter to be packed through and across the width of the fusion implant, thereby enabling rapid fusion through the implant.

Figure 48:
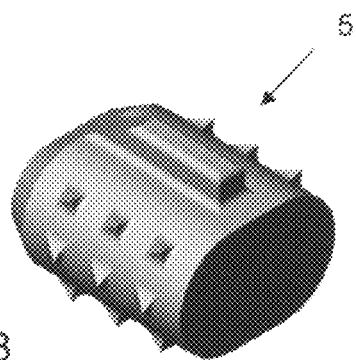
Figure 49:
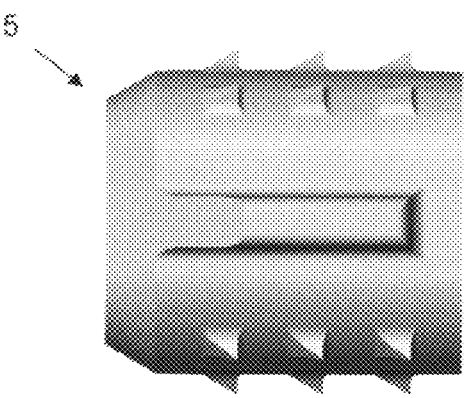
Figure 50:
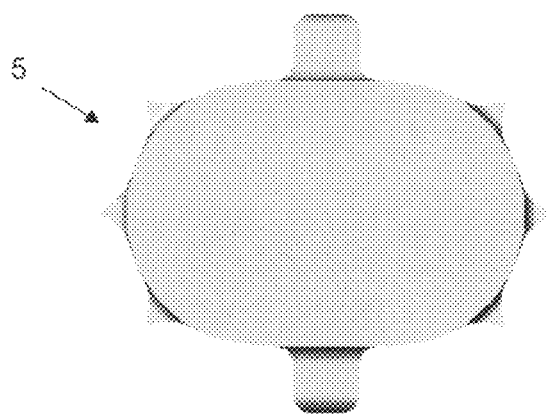
Figure 51:
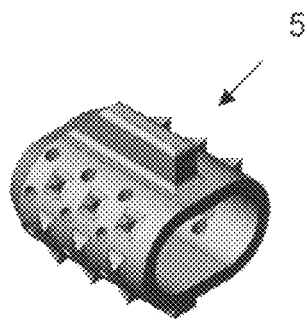
Figure 52:
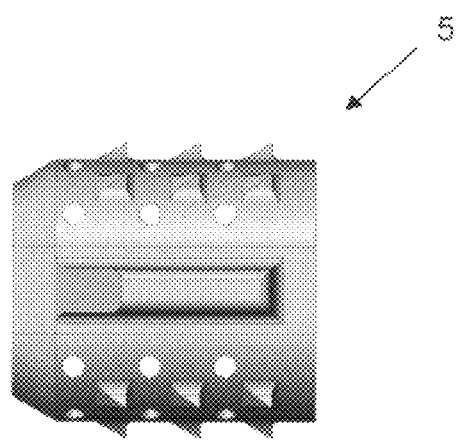
Figure 53:
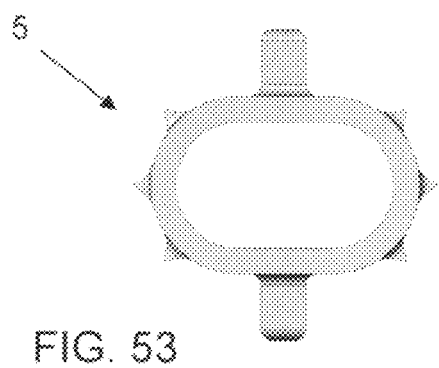
Figure 54:
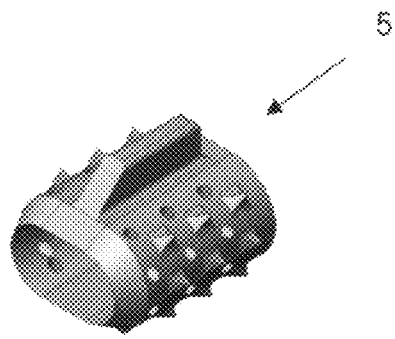

FIGS. 48-50 illustrate a fusion implant 5 which is similar to the implant of FIGS. 29-31. However, in this embodiment, the grooves are replaced with barbs (i.e., forward biting teeth) extending around the surface of the body.

FIGS. 51-54 illustrate a fusion implant 5 which is similar to the embodiment shown in FIGS. 48-50, however, the fusion implant comprises a hollow body having an internal cavity and plurality of openings extending through the side wall of the body and communicating with the cavity.

Figure 55:
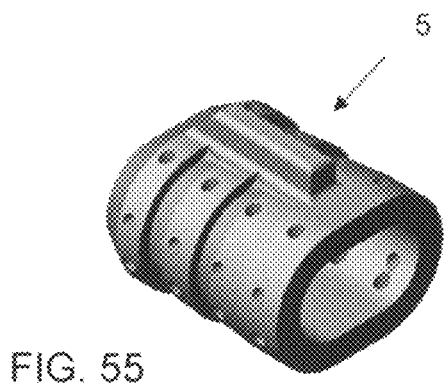
Figure 56:
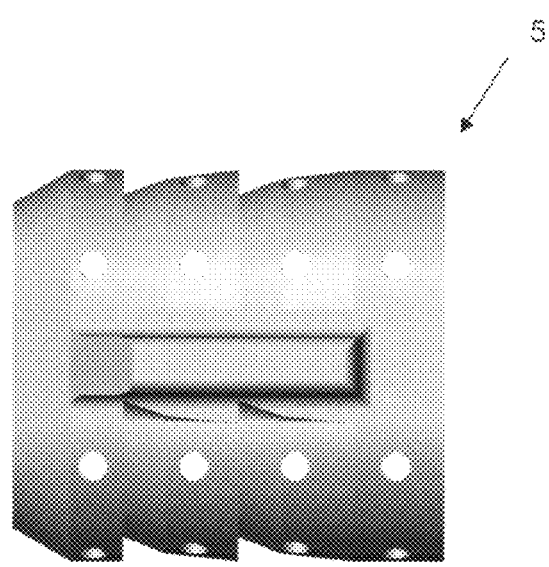
Figure 57:
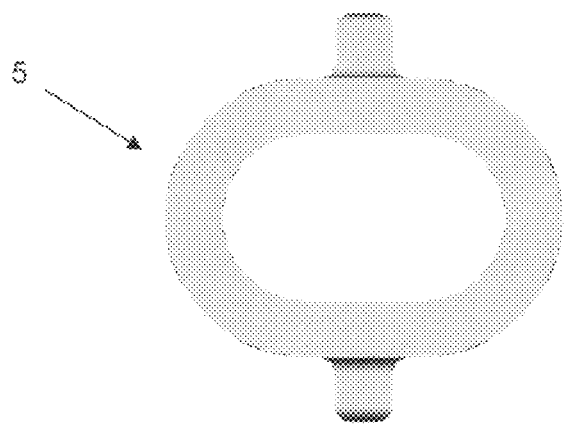

FIGS. 55-57 illustrate a fusion implant 5 which is similar to the embodiment shown in FIGS. 29-31, however, the fusion implant comprises a hollow body having an internal cavity and plurality of openings extending through the side wall of the body and communicating with the cavity.

Figure 58:
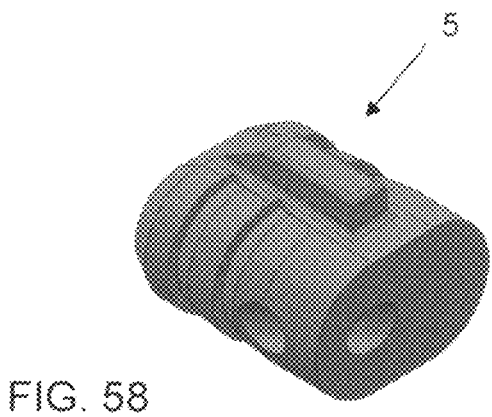
Figure 59:
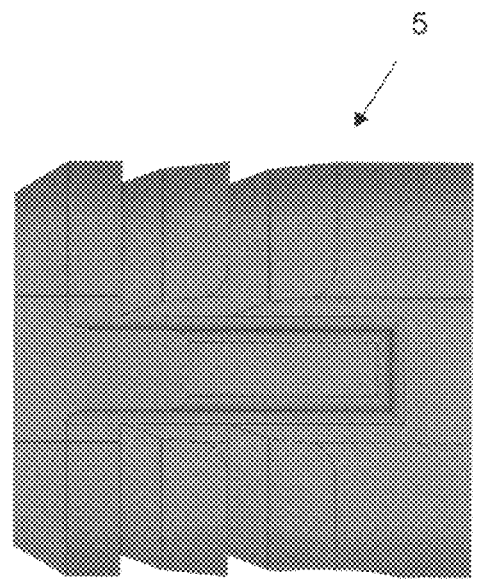
Figure 60:
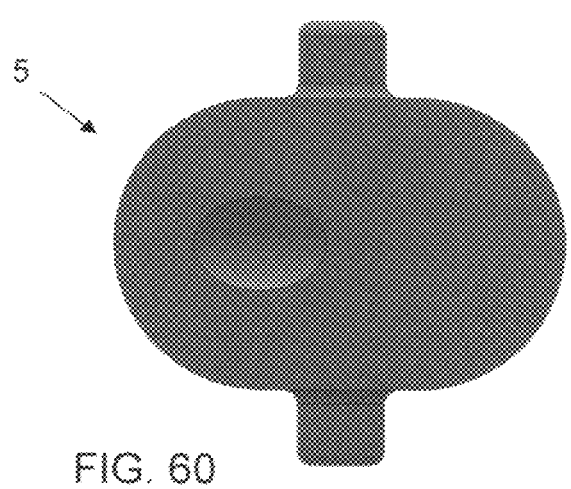
Figure 61:
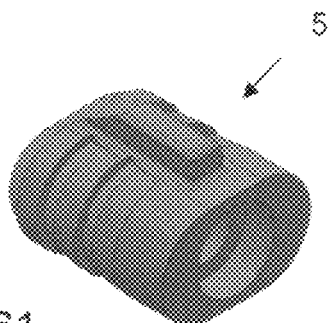
Figure 62:
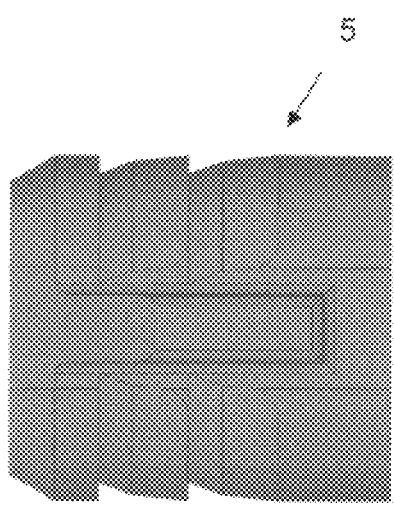
Figure 63:
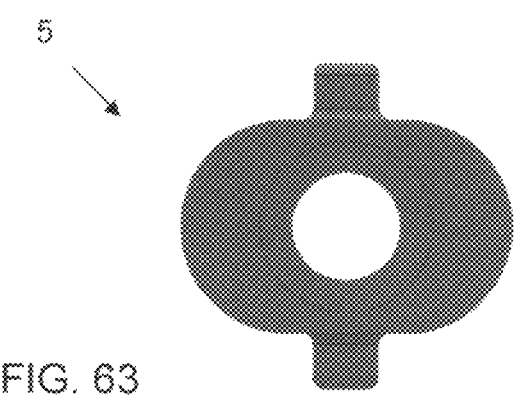
Figure 64:
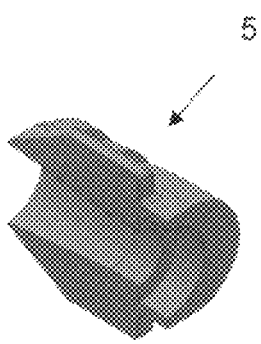
Figure 65:
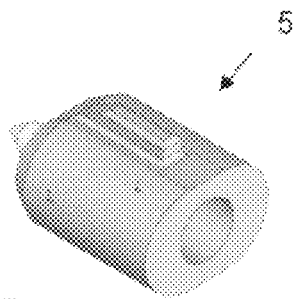
Figure 66:
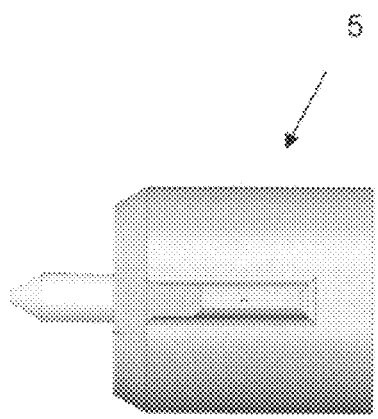
Figure 67:
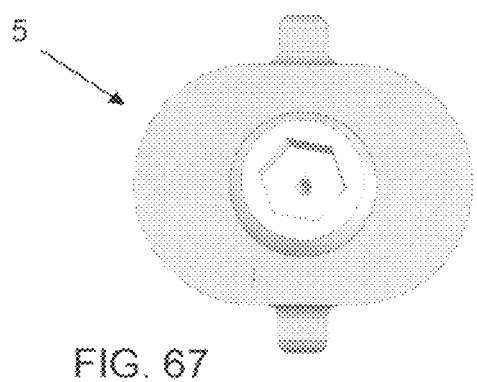
Figure 68:
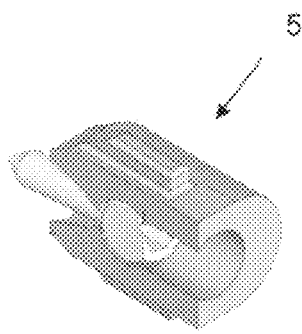

FIGS. 58-60 illustrate a fusion implant 5 which is similar to the embodiment shown in FIGS. 29-31 and further comprises a hole for attaching the implant to the facet joint. The attachment may be effected by K-Wire, suture, staple, screw or other fixation device.

FIGS. 61-64 illustrate a fusion implant 5 which is similar to the embodiment shown in FIGS. 29-31 and further comprises a hole for attaching the implant to the facet joint. The attachment may be effected by K-Wire, suture, staple, screw or other fixation device. Preferably, a screw is used to attach the implant to the facet joint.

FIGS. 65-68 illustrate a fusion implant 5 which is similar to the embodiment shown in FIGS. 29-31 and further comprises a hole for attaching the implant to the facet joint. The attachment may be effected by an integrated screw. Like FIGS. 29-31, this embodiment may also comprise grooves.

FIGS. 69-71 illustrate a fusion implant 5 which is similar to the embodiment shown in FIGS. 29-31 and further comprises rectangular, sharp spikes for attaching the implant to the facet joint.

Figures 72, 73, 74:
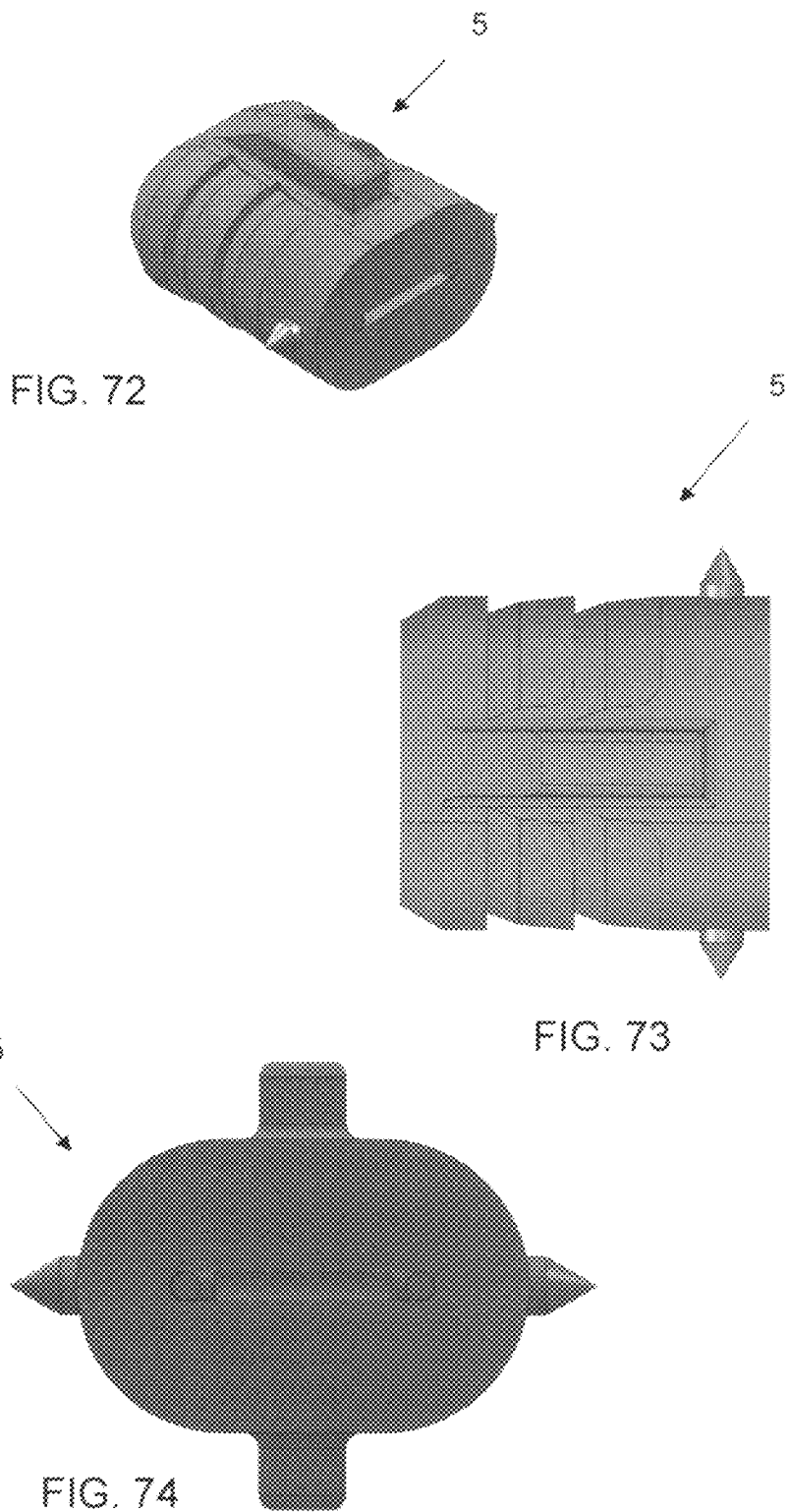

FIGS. 72-74 illustrate a fusion implant 5 which is similar to the embodiment shown in FIGS. 29-31 and further comprises round, sharp spikes for attaching the implant to the facet joint.

ADVANTAGES OF THE INVENTION

Numerous advantages are achieved by the present invention. Among other things, the present invention provides a fast, simple, minimally-invasive and easily reproduced approach for effecting facet fusion.

Applications to Joints Other than Facet Joints

While fusion implant 5 has been discussed above in the context of fusing a facet joint, it should also be appreciated that fusion implant 5 may be used to stabilize and fuse any joint having anatomy similar to the facet joint, i.e., a pair of opposing bony surfaces defining a gap therebetween, with the stabilizer of the fusion implant being sized to be positioned within the gap. By way of example but not limitation, the fusion implant may be used in small joints such as the fingers, toes, etc.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A spinal facet fusion implant comprising:
   an elongated body having a distal end, a proximal end and a longitudinal axis extending between the distal end and the proximal end, the elongated body having a transverse cross-sectional profile characterized by a primary axis disposed perpendicular to a transverse axis of said elongated body and a secondary axis disposed perpendicular to the primary axis and perpendicular to the transverse axis;
   at least one stabilizer formed integral with the elongated body and extending radially outwardly from the elongated body in the secondary axis, the at least one stabilizer extending along at least a portion of a length of the elongated body;
   wherein the elongated body has a dimension along the primary axis which is less than a combined width of opposing spinal facets that collectively form a facet joint, and wherein the elongated body has a dimension along the primary axis which is greater than a gap located between said opposing spinal facets, such that, when appropriate recesses are formed in the opposing spinal facets, the elongated body can be inserted between opposing spinal facets so that segments of the elongated body disposed along the primary axis can span said gap and sit in corresponding recesses formed in the opposing spinal facets;
   and further wherein the at least one stabilizer has a dimension in a direction extending parallel to the primary axis which is sized to make a press fit into said gap.

2. A spinal facet fusion implant according to claim 1 wherein the elongated body is chamfered at said distal end.

3. A spinal facet fusion implant according to claim 1 wherein the elongated body comprises at least one barb on its outer surface, wherein the barb is configured to permit axial insertion in the distal direction and inhibit axial retraction in the proximal direction.

4. A spinal facet fusion implant according to claim 1 wherein the elongated body is substantially solid.

5. A spinal facet fusion implant according to claim 4 wherein the elongated body includes at least one opening therein to permit bone in-growth.

6. A spinal facet fusion implant according to claim 5 wherein the at least one opening comprises a cross-bore.

7. A spinal facet fusion implant according to claim 5 wherein the at least one opening comprises a blind hole.

8. A spinal facet fusion implant according to claim 5 wherein the at least one opening is filled with a bone growth promoter.

9. A spinal facet fusion implant according to claim 1 wherein the elongated body is substantially hollow.

10. A spinal facet fusion implant according to claim 9 wherein the elongated body includes at least one opening therein to permit bone in-growth.

11. A spinal facet fusion implant according to claim 10 wherein the at least one opening comprises a cross-bore.

12. A spinal facet fusion implant according to claim 10 wherein the at least one opening comprises a blind hole.

13. A spinal facet fusion implant according to claim 10 wherein the at least one opening is filled with a bone growth promoter.

14. A spinal facet fusion implant according to claim 1 wherein the elongated body comprises at least one surface groove.

15. A spinal facet fusion implant according to claim 14 wherein the surface groove extends parallel to the longitudinal axis.

16. A spinal facet fusion implant according to claim 14 wherein the surface groove extends perpendicular to the longitudinal axis.

17. A spinal facet fusion implant according to claim 14 wherein the surface groove extends transverse to the longitudinal axis.

18. A spinal facet fusion implant according to claim 14 wherein the length of the primary axis is greater than the length of the secondary axis.

19. A spinal facet fusion implant according to claim 1 wherein the length of the secondary axis is greater than the length of the primary axis.

20. A spinal facet fusion implant according to claim 1 wherein the cross-sectional profile is non-circular.

21. A spinal facet fusion implant according to claim 1 wherein the cross-sectional profile is rectangular.

22. A spinal facet fusion implant according to claim 1 wherein the cross-sectional profile is rounded rectangular.

23. A spinal facet fusion implant according to claim 1 wherein the cross-sectional profile is ovoid.

24. A spinal facet fusion implant according to claim 1 wherein the cross-sectional profile is triangular.

25. A spinal facet fusion implant according to claim 1 wherein the cross-sectional profile is circular.

26. A spinal facet fusion implant according to claim 1 wherein the at least one stabilizer extends upwardly from the elongated body.

27. A spinal facet fusion implant according to claim 1 wherein the at least one stabilizer extends downwardly from the elongated body.

28. A spinal facet fusion implant according to claim 1 wherein the fusion implant comprises a pair of stabilizers.

29. A spinal facet fusion implant according to claim 28 wherein the pair of stabilizers are diametrically opposed relative to one another.

30. A spinal facet fusion implant according to claim 1 wherein the spinal facet fusion implant further comprises a fixation device for securing the spinal facet fusion implant in the facet joint.

31. A spinal facet fusion implant according to claim 30 wherein the fixation device comprises a screw.

32. A method for fusing a spinal facet joint, the method comprising the steps of:
    providing a spinal facet fusion implant comprising:
       an elongated body having a distal end, a proximal end and a longitudinal axis extending between the distal end and the proximal end, the elongated body having a transverse cross-sectional profile characterized by a primary axis disposed perpendicular to said transverse axis and a secondary axis disposed perpendicular to the primary axis and disposed perpendicular to said transverse axis; and
       at least one stabilizer formed integral with the elongated body and extending radially outwardly from the elongated body in the secondary axis, the at least one stabilizer extending along at least a portion of a length of the elongated body;
       wherein the elongated body has a dimension along the primary axis which is less than a combined width of opposing spinal facets collectively forming a facet joint, and wherein the elongated body has a dimension along the primary axis which is greater than a gap located between said opposing spinal facets, such that, when appropriate recesses are formed in said opposing spinal facets, the elongated body is inserted between opposing spinal facets so that segments of the elongated body disposed along the primary axis span the gap located between the opposing spinal facets and sit in corresponding recesses formed in said opposing spinal facets; and further wherein the at least one stabilizer has a dimension in a direction extending parallel to the primary axis which is sized to make a press fit into the gap between said opposing spinal facets;

deploying the spinal facet fusion implant in the facet joint so that the elongated body is simultaneously positioned within both of said opposing facets and the at least one stabilizer is positioned within the gap between said opposing spinal facets; and maintaining the spinal facet fusion implant in said position while fusion occurs.

33. A method according to claim 32 wherein the spinal facet fusion implant is installed in a cavity which is preformed in said opposing spinal facets.

34. A method according to claim 32 wherein the spinal facet fusion implant is installed into the virgin bone of the spinal facets.

* * * * *